(12) United States Patent
Regittnig et al.

(10) Patent No.: US 9,320,851 B2
(45) Date of Patent: Apr. 26, 2016

(54) INFUSION ARRANGEMENT AND METHOD

(71) Applicant: Medizinische Universitaet Graz, Graz (AT)

(72) Inventors: Werner Regittnig, Graz (AT); Miró Jungklaus, Graz (AT)

(73) Assignee: Medizinische Universitaet Graz, Graz (AT)

( * ) Notice: Subject to any disclaimer, the term of this patent is extended or adjusted under 35 U.S.C. 154(b) by 176 days.

(21) Appl. No.: 14/174,799

(22) Filed: Feb. 6, 2014

(65) Prior Publication Data

US 2014/0221965 A1    Aug. 7, 2014

Related U.S. Application Data

(60) Provisional application No. 61/762,229, filed on Feb. 7, 2013.

(51) Int. Cl.
  *A61M 5/168*    (2006.01)
  *A61M 5/172*    (2006.01)
  *A61M 5/142*    (2006.01)

(52) U.S. Cl.
  CPC ....... *A61M 5/16836* (2013.01); *A61M 5/14244* (2013.01); *A61M 5/16854* (2013.01); *A61M 5/16877* (2013.01); *A61M 5/16886* (2013.01); *A61M 5/1723* (2013.01); *A61M 2005/14208* (2013.01); *A61M 2005/1726* (2013.01); *A61M 2205/3334* (2013.01); *A61M 2205/3344* (2013.01); *A61M 2230/005* (2013.01)

(58) Field of Classification Search
  CPC .................. A61M 5/1723; A61M 2005/1726; A61M 2205/3344; A61M 5/16854; A61M 2037/0007; A61M 5/16831; A61M 2230/005; A61M 5/16836; A61M 5/16877; A61M 5/16886; A61M 5/16859
  See application file for complete search history.

(56) References Cited

U.S. PATENT DOCUMENTS

| 4,191,184 | A | * | 3/1980 | Carlisle ............ A61M 5/16809 128/DIG. 12 |
| 5,087,245 | A | * | 2/1992 | Doan ................ A61M 5/16859 128/DIG. 12 |
| 5,190,748 | A | * | 3/1993 | Bachynsky .......... A61K 9/4858 424/78.08 |
| 5,356,378 | A | | 10/1994 | Doan |
| 5,501,665 | A | | 3/1996 | Jhuboo et al. |
| 6,007,520 | A | * | 12/1999 | Sudo ......................... A61J 1/10 264/496 |
| 2003/0060753 | A1 | | 3/2003 | Starkweather et al. |
| 2004/0120825 | A1 | | 6/2004 | Bouton et al. |
| 2004/0215080 | A1 | * | 10/2004 | Lechner ................ A61B 5/032 600/463 |

(Continued)

FOREIGN PATENT DOCUMENTS

| EP | 0 248 633 B1 | 8/1994 |
| EP | 1 342 481 B1 | 10/2009 |

(Continued)

*Primary Examiner* — Nathan R Price
*Assistant Examiner* — William Carpenter
(74) *Attorney, Agent, or Firm* — Robert A. Blaha; Smith Tempel Blaha LLC

(57) ABSTRACT

An arrangement for administering a predetermined amount of a substance into an organism is presented. The arrangement includes a member adapted to provide information indicative of a tissue resistance against flow of a fluid containing the substance upon administration into the tissue and a controller adapted to adjust an administration characteristic of the fluid based on the information such as to achieve an intended absorption rate of the substance.

16 Claims, 13 Drawing Sheets

(56) References Cited

U.S. PATENT DOCUMENTS

| | | | |
|---|---|---|---|
| 2005/0065470 A1* | 3/2005 | Reed | A61M 1/0003 604/122 |
| 2006/0122555 A1 | 6/2006 | Hochman | |
| 2007/0219480 A1 | 9/2007 | Kamen et al. | |
| 2008/0114218 A1 | 5/2008 | Suyama et al. | |
| 2008/0154188 A1* | 6/2008 | Hochman | A61C 19/08 604/67 |
| 2009/0270790 A1* | 10/2009 | Raghavan | A61M 37/00 604/22 |
| 2009/0326439 A1 | 12/2009 | Chomas et al. | |
| 2010/0152644 A1* | 6/2010 | Pesach | A61M 37/0092 604/20 |
| 2010/0274202 A1* | 10/2010 | Hyde | A61B 5/1405 604/272 |
| 2011/0160697 A1* | 6/2011 | Yodfat | A61B 18/14 604/506 |

FOREIGN PATENT DOCUMENTS

| | | |
|---|---|---|
| WO | WO 9505864 A1 | 3/1995 |
| WO | WO 9608288 A1 | 3/1996 |
| WO | WO9801168 A2 | 1/1998 |
| WO | WO 0013726 A1 | 3/2000 |
| WO | WO 0172357 A2 | 10/2001 |
| WO | WO03000146 A1 | 1/2003 |
| WO | WO 03023708 A2 | 3/2003 |
| WO | WO 2005065146 A2 | 7/2005 |
| WO | WO 2007092618 A2 | 8/2007 |
| WO | WO2008114218 A2 | 9/2008 |
| WO | WO 2009081262 A1 | 7/2009 |
| WO | WO2010023666 A2 | 3/2010 |
| WO | WO 2010052579 A2 | 5/2010 |
| WO | WO 2011091246 A2 | 7/2011 |
| WO | WO2013062225 A1 | 2/2013 |

* cited by examiner

INFUSION ARRANGEMENT AND METHOD

CROSS-REFERENCE TO RELATED APPLICATIONS

The benefit of the filing date of U.S. Provisional Patent Application No. 61/762,229, filed Feb. 7, 2013, entitled "Infusion Arrangement and Method," is hereby claimed and the specification thereof incorporated herein in its entirety by this reference.

TECHNICAL FIELD

The present invention relates to an arrangement and to a method for administering a substance into an organism.

BACKGROUND

Patients suffering from diabetes, in particular type 1 diabetes, require insulin replacement therapy to compensate for the loss of their pancreatic islet cells. The goal in this therapy is to maintain glucose levels in the normal range by replicating the physiological pattern of insulin secretion of the healthy pancreas, thereby avoiding short-term complications (i.e., hypoglycaemia or hyperglycaemia with ketosis and osmotic diuresis) as well as long-term vascular complications (e.g., renal failure, blindness, myocardial infarction, stroke, limb amputation). At present, the vast majority of type 1 diabetic patients self-administer insulin either by a subcutaneous bolus injection using a hypodermic needle (e.g., syringe, insulin pen) or by a subcutaneous infusion using an indwelling catheter connected to an insulin pump (insulin pump therapy). In addition, to guide adjustments in insulin dosage, food consumption and physical activity, people with type 1 diabetes self-monitor blood glucose levels by typically measuring glucose in blood obtained using finger-pricking. In the treatment of diabetes using an infusion apparatus, such as an insulin pump, insulin is usually administered at a high rate before meals (bolus insulin delivery) and at a low rate after meals and during night (basal insulin delivery). Most current insulin pumps deliver the basal insulin as small pulses with relatively long time intervals between pulses (up to several minutes). The bolus insulin, however, is usually delivered as macro-pulses with a high repetition frequency of the pulses (pulse intervals equal to or smaller than four seconds). Thus, the length of a bolus delivery period (bolus duration) usually depends on the bolus size (e.g. total volume or total mass) chosen by the patient and on the repetition frequency and magnitude of the macro-pulses employed in the insulin pump. For example, a typical bolus amount may be ten to fifteen units of insulin. Thus, when insulin pump models with high pulse frequency and/or large pulse sizes are used, then a typical bolus amount of insulin is administered during a time span of one minute or less. However, with insulin pump models featuring smaller pulse sizes and/or lower pulse frequency, typical bolus amounts of insulin are delivered over a longer time span (e.g., 10 min), in order to prevent burning sensation at the infusion site, to delimit the power consumption or the like.

In the treatment of diabetes using an insulin pump, the insulin is infused into the tissue through an indwelling catheter (e.g., Teflon cannula or steel needle). A general recommendation of drug and device manufacturers is to change the indwelling catheter and the infusion site every 2-3 days in order to avoid infection and lipohyperthrophy at the infusion site as well as deterioration in control of the blood glucose concentration due to reduced insulin absorption. It has been shown that there is considerable inter- and intra-individual variability in the length of use of the indwelling catheters and infusion sites and that in a large group of diabetic patients the duration of use of catheter and infusion site can be safely prolonged beyond the recommended 2-3 day period. Thus, in order to improve the therapy with insulin pumps and to reduce costs associated with this therapy, it would be desirable to individually determine the longest possible duration of use of a particular infusion site and to alert the patient to change the indwelling catheter and the infusion site when the maximum usage duration is reached.

Furthermore, it has been previously shown that the insulin absorption rate following subcutaneous administration of a bolus amount of insulin is associated with a large inter- and intra-individual variability, which may arise from various exogenous factors including injection technique, infusion pressure and bolus length applied in the insulin pump, as well as endogenous factors including tissue geometry, convective and diffusive transport of the insulin in the tissue, and tissue blood flow. In addition, it has been observed that, when a bolus amount of insulin is injected or infused into the subcutaneous tissue, the subcutaneous insulin absorption from the administration site into the blood is much slower than the insulin secretion from the healthy pancreas into the blood.

These and other limitations may make it difficult for type 1 diabetic patients to achieve physiologic insulin replacement patterns and, consequently, glycemic control is frequently insufficient in these patients. Therefore, rates of co-morbidity and mortality continue to be greatly elevated in type 1 diabetic patients.

SUMMARY

Thus, there may be a need for an arrangement and a method for administering a predetermined amount of a substance, wherein an absorption of the substance from a desired organ or tissue into the blood stream is improved or increased and wherein a variability of the absorption of the substance is decreased. Further, there may be a need for an arrangement for administering insulin which may allow a faster absorption of the insulin from the administration site into the blood stream and may also reduce the variability in the absorption of the insulin.

In addition, there may be a need for an arrangement and a method for determining the longest possible duration of use of a tissue site for the administration of the substance.

According to an embodiment of the present invention it is provided an arrangement for administering a predetermined amount of a substance into an organism, the arrangement comprising: a member adapted to provide information indicative of a tissue resistance against flow of a fluid containing the substance upon administration into the tissue; and a controller adapted to adjust an administration characteristic of the fluid based on the information such as to achieve a predetermined absorption rate of the substance.

The arrangement for administering the predetermined amount of the substance (in particular insulin) may in particular be embodied as an infusion system comprising one or more components, such as a reservoir, a pump unit, a conduit, a tubing and a cannula, for example. The infusion system may be embodied also as a pen-like administration device.

The member which is adapted to provide information indicative of a tissue resistance against the flow of the fluid may be adapted to either gather or generate or acquire the information, in particular in this case the member may comprise a sensor, such as a pressure sensor. Alternatively or additionally, the member may hold the information in a storage medium and is adapted to access this information.

According to an embodiment of the present invention the administration characteristic comprises at least one definition of an (controllable) exogenous factor relating to: a total administration duration being a total time duration over which fluid is continuously or repeatedly in a pulse wise manner administered; an administration pulse duration being a time interval over which fluid is continuously administered with a particular flow rate; an administration pulse height being a flow rate with which the fluid is continuously administered during the administration pulse duration; an administration pulse frequency being the number of administration pulses per time unit employed to administer the fluid during the total administration duration; an administration pulse shape being a time course of a flow rate with which the fluid is administered during the administration pulse duration; an anatomical location of the administration site where the fluid is administered into the organism; a duration of use of the administration site for administering the fluid into the organism.

The controller may be adapted to define one or more of these (controllable) exogenous factors based on the information of the tissue resistance such as to achieve the intended absorption rate of the substance. In particular the controller may indicate to the user (such as by displaying a recommendation, giving a warning etc.), when an anatomical location of the administration site should be changed.

The tissue resistance may be an easily measurable parameter that provides quantitative information both on the morphological and structural properties of the tissue and on the tissue-specific transport properties for the substance-containing fluid. In general, insulin absorption may strongly depend on the anatomical location of the administration site. For example, insulin absorption may be faster from the abdomen than from the thigh and that, within the upper arm area, insulin absorption may be faster after perpendicular injection without folding the skin than after injections into a skinfold with angling the injection needle at 45°. Furthermore, within the abdominal region, insulin absorption may be considerably faster from the upper than the lower abdomen, and that subcutaneous insulin absorption may be considerably faster with prolonged use of an insulin infusion site. These variations in the subcutaneous insulin absorption may be explained by variations in the tissue structure and/or changes in the insulin transport efficiency in the tissue at the administration site. Thus, as tissue structure and transport efficiency may be strongly correlated with the tissue resistance, variations and changes in these tissue properties may be reflected as changes in the size of the tissue resistance.

When a fluid containing the substance is injected or infused into a tissue, the fluid and substance may spread or distribute in a tissue area around the infusion or administration site. In general, the initial area of distribution (initial distribution volume) of the infused substance in the tissue at the administration site and its subsequent absorption may depend on controllable exogenous factors, like the volume of the substance-containing fluid infused, and the employed infusion rate (or total administration duration), as well as on (in particular uncontrollable) endogenous factors, like the convective and diffusive transport properties for the substance in the tissue at the administration site, and the morphological and structural properties of the tissue, of which the most important may be the fractional volumes of the three tissue compartments, i.e., the relative spaces taken by the interstitium, blood vessels (mainly capillaries), and cells. Thus, because major endogenous factors may be strongly reflected in the measurable tissue resistance, the distribution volume and absorption rate of the administered substance may be reliably predicted from the chosen settings of the controllable exogenous factors and the determined tissue resistance. Furthermore, by adjusting the exogenous factors (or administration characteristic) based on the determined tissue resistance value, a desired or predetermined distribution volume and absorption rate of the substance at the administration site may be obtained.

As the tissue cells may act as relatively impervious obstacles to substance diffusion and fluid flow due to the low permeability and hydraulic conductance of the cell membranes, the transport processes affecting the distribution of the infused substance in the tissue may mainly be the convective and diffusive transport through the interstitial space and also the convective and diffusive transport across micro-vascular walls into the blood vessels.

Thereby, the diffusive transport of substances in the interstitial space and across the micro-vascular walls may be governed by the substance concentration gradients, the diffusion coefficient of the substance in the interstitial space and also the permeability of the micro-vascular walls to the substance. In particular, the substance concentration gradient across the vascular wall may also depend on the blood flow in the tissue. In addition, the diffusion and permeability coefficients for larger substances like insulin may take significantly lower values than that of smaller substances like glucose.

Further, the convective transport of fluids and substances in the interstitial space and across the micro-vascular walls may depend on the pressure gradients in the interstitial space and across the vessel walls, the hydraulic conductivity in the interstitial space, the vascular conductivity, the interstitial retardation factor and the filtration reflection factor of the micro-vascular wall. Thereby, a filtration reflection factor of one may represent a completely impermeable barrier, while a filtration reflection factor of zero may refer to a freely permeable barrier. In addition, the interstitial retardation factor may be defined as the relative velocity of a substance (e.g. insulin) with respect to the fluid velocity. This interstitial retardation factor may take values less than one, as a substance velocity may be assumed to be generally slower than the fluid velocity due to the interactions between the substance and tissue structures, like the interstitial network of collagen fibrils, elastin and fibrous molecules. Thus, high molecular weight substances, like insulin, may have higher filtration reflection factors and lower interstitial retardation factors than substances of low molecular weight. Due to that, the absorption of subcutaneously injected substances of larger size may be much slower compared to the absorption of substances of smaller size. For example, it may take several hours for the subcutaneous absorption of 70% of a typical bolus amount of a short-acting insulin (~0.1 ml of a 100-unit/ml insulin solution), whereas it may take just five minutes for the absorption of 70% of 0.08 ml of pure water following injection into the subcutaneous tissue.

An important controllable exogenous factor that strongly influences subcutaneous substance absorption may be the bolus duration (also referred to as total administration duration). This exogenous factor may be used (in particular changed) by the controller to adjust the tissue distribution volume and rate of absorption of an administered substance. For example, during bolus administration of an high molecular weight substance, in particular insulin, with a relatively long bolus duration, such as ten minutes, fluid absorption, in particular water absorption, may be very large, which may result in a diminished convective fluid flow in the surrounding of the infusion site. Further, as the filtration reflection factor of the subcutaneous vasculature for the high molecular weight substance may be very high, molecules of this substance may accumulate in the vicinity of the infusion site. In contrast, during bolus administration of the high molecular weight substance, in particular insulin, with relatively short bolus duration, such as for example 0.5 min, fluid absorption, in particular water absorption, may be much less significant, which may in turn increase the interstitial conductive flow in the surrounding of the infusion site, thereby causing the substance molecules to distribute in a larger volume of the tissue surrounding the infusion site when compared to a administration of the bolus over a relatively long time. Further, a larger distribution volume may expose a higher number of capillaries to the high molecular weight substance, in particular insulin, thereby increasing the absorption of the substance.

Pressure gradients established in the fluid delivery conduit during a bolus delivery period (total administration duration) may strongly depend on the magnitude of the macro-pulses (also referred to as administration pulse height) and repetition frequency (also referred to as administration pulse frequency) employed in the infusion system. For example, if the pulse repetition frequency is fixed to one pulse every three seconds, a 10 µl fluid pulse introduced over one second may induce a higher pressure peak (and in particular higher absorption) than a 10-µl fluid pulse introduced over two seconds. Further, pressure gradients established during the delivery of the predetermined amount of the substance may cause a deformation of the tissue, which in turn may cause pressure-dependent changes in the transport parameters.

Therefore, besides the bolus duration, the pulse shape (also referred to as administration pulse shape) and pulse repetition frequency (also referred to as administration pulse frequency) employed during the bolus delivery period (total administration duration) may also influence the tissue distribution volume and absorption rate of the administered substance. Therefore, the magnitude, duration and repetition frequency of the fluid pulses may be other important exogenous factors that can be used (in particular adapted or changed) by the controller to adjust the tissue distribution and absorption of the substance, in particular insulin.

According to an embodiment of the present invention the arrangement further comprises a pump adapted to be coupled to a reservoir holding the fluid containing the substance and adapted to drive the substance-containing fluid; a conduit, in particular comprising a flexible tubing, for guiding the liquid driven by the pump from the reservoir into the tissue, the conduit having one end, in particular formed by a cannula, insertable into the tissue and having another end coupled to the pump unit, wherein the controller is adapted to control the pump to adjust the flow rate of the fluid to comply with the adjusted administration characteristic.

The reservoir may in particular be in form of a syringe or may take any other shape or structure which is suitable for storing or receiving or accommodating the liquid. The cannula may comprise a biocompatible material, in which in particular an insertion needle is insertable. Further, the insertion needle may only be located within the lumen of the cannula during inserting the cannula into the tissue of the organism. After inserting the cannula into the tissue of the organism, the insertion needle may be withdrawn from the lumen of the cannula. Afterwards, the fluid containing the substance may be conveyed within the conduit, in particular within the lumen of the conduit, from the reservoir to the exit end of the cannula, which has been inserted into the tissue of the organism. Providing a pump and a conduit may reproducibly convey the fluid to the infusion site. The pump may for example comprise an electric motor.

According to an embodiment of the present invention the member (adapted to provide information indicative of the tissue resistance) comprises a pressure sensor and is adapted to measure and/or to store, in particular in an electronic storage medium, a pressure of the fluid in the conduit.

The pressure in the conduit (which may evolve, when the pump is operated at a particular power or when the flow rate has a particular value) may be easily measured using the pressure sensor and the pressure may be used to derive the information indicative of the tissue resistance. Thereby, the arrangement may be simplified and the arrangement may be enabled to acquire or measure quantities which may allow the information indicative of the tissue resistance to be determined or derived therefrom.

According to an embodiment of the present invention the pressure sensor is located at the pump, at the reservoir, or at a location along the conduit, in particular at or close to the one end or the other end of the conduit. Thereby, a construction flexibility of the arrangement is increased. When the pressure sensor is located for example at the pump a high accuracy pressure sensor which may be relatively expensive, may be used, as this pressure sensor is not required to be replaced each time a new infusion site is selected or each time a new infusion process is initiated. On the other hand, when the pressure sensor is arranged at the reservoir, at the conduit or on the conduit, the pressure sensor may be required to be replaced, since the conduit itself may be replaced each time a new infusion site is selected and/or a new infusion process is initiated. In other embodiments the reservoir may be replaced together with the cannula and the tubing.

According to an embodiment of the present invention the arrangement is adapted, using the pressure sensor, to determine a pressure difference based on a first pressure measurement, when the one end of the conduit is inserted into the tissue, and a second pressure measurement, when the one end of the conduit is external to the tissue, in particular at atmosphere, wherein the arrangement is further adapted to obtain the tissue resistance based on the determined pressure difference, in particular as a time average of the pressure difference, in particular proportional to the pressure difference. Thereby, particular a hydrostatic pressure of the liquid during the first pressure measurement and/or the second pressure measurement is taken into account for calibration or the hydrostatic pressure of the liquid during the first pressure measurement and/or the second pressure measurement is held constant.

During the first pressure measurement and the second pressure measurement, the pump may be operated at a particular power or flow rate of the liquid. The second pressure measurement may be performed before or after the first pressure measurement. In particular, the second pressure measurement may be performed before and after the first pressure measurement and an average of the two second pressure measurements may be determined. The second pressure measurement may in particular account for a system resistance defining a resistance to the flow of the liquid due to the arrangement comprising the pump, the reservoir and the conduit not being inserted within the tissue of the organism. The first pressure measurement, in contrast, may account for the resistance properties of the tissue and additionally the system resistance. Thus, the value obtained by taking a difference between the pressure measured in the first pressure measurement and the pressure measured in the second pressure measurement, may be indicative of the tissue resistance alone. In particular, a time average of the pressure difference may be taken or calculated or computed during the entire administration of the predetermined amount of the substance (and the flow rate may be adjusted continuously).

In particular there are a number of possibilities to perform the second pressure measurement (also referred to as system reference measurement or system void measurement): 1) For the used infusion set and reservoir the second measurement may be performed by the manufacturer of the arrangement. The thus measured system reference resistance may be stored in a storage, e.g. comprised in the controller or the pump. Thereby no additional second measurement is necessary when the arrangement is used to administer the liquid to the organism. 2) Alternatively or additionally, the second pressure measurement may be performed before inserting the cannula, in particular during filling the pipe or tubing with the liquid containing the substance, in particular insulin.

In particular there are a number of possibilities to perform the first pressure measurement (also referred to as system-tissue measurement): 1) The first pressure measurement may be performed during basal insulin administration (thus basic insulin administration over the day unrelated to a meal) or 2) at the beginning of the bolus administration of insulin (i.e. meal related administration). For the measurement during basal insulin administration, small insulin administration pulses, which may e.g. be delivered every some minutes, may be used during which first pressure measurements are performed. For the measurement at the beginning of the bolus administration the first one, first two or a few of the first pulses may be used during which first pressure measurements may be performed. Based on these measurements the next pulses may be adjusted regarding pulse duration, pulse shape, pulse frequency etc.

The accuracy or precision of the first and the second measurement and the precision of the difference between the first measurement and the second measurement may depend on the characteristic (height, shape, duration etc.) of the pulses during which the measurements were performed. In general, relatively short duration and high-height pulses may result in relatively high pressure than long duration and low-height pulses. Relatively short duration and high-height pulses may be advantageous, since (small) occasional pressure perturbances, such as those resulting from movement of the organism or parts of the organism, may not have a significant influence on the accuracy. Thereby appropriate selection of the characteristic of the pulses during the measurements may improve the accuracy of the measurements.

If the reservoir containing the liquid is located vertically higher (or lower) than the infusion site, then the pressure of the liquid within the conduit may be higher (lower) than the pressure generated by the pump alone (its hydrostatic pressure). When the tissue resistance is measured, the hydrostatic pressure of the liquid should be taken into account. In particular, the hydrostatic pressure may be held constant (at a fixed value) during the first measurement and second measurement. Alternatively, if there is a difference in the hydrostatic pressure observed in the first measurement compared with that in the second measurement, this difference in the hydrostatic pressure may be taken into account when deriving the tissue resistance from the pressure values obtained during the first and second measurement.

According to an embodiment of the present invention the controller is adapted to adjust the flow rate of the liquid during the first measurement and during the second measurement to a same value. The tissue resistance (TR which may have units $kPa \cdot s \cdot mm^{-3}$ i.e. pressure times time divided by volume) may then be calculated as $TR = \Delta P/FR$, where FR is the flow rate of the liquid in $mm^3/s$ (or $\mu l/s$) (i.e. volume per time) and $\Delta P$ may be the difference in the pressure values from the first and second measurement (in kPa). In particular, because the tissue resistance calculated in this way may depend on the cross-sectional area of the conduit or cannula applied for substance delivery, it may be advantageous to first normalize the flow rate of the liquid for the cross-sectional area of the conduit end or cannula end at the delivery site (A; in $mm^2$) and then calculate a specific tissue resistance (STR; in $Pa \cdot s \cdot mm^{-1}$) as $STR = \Delta P/(FR/A) = (\Delta P \cdot A)/FR$. Thereby, the specific tissue resistance obtained for a delivery site may refer to a pressure gradient per unit flow of a specified liquid across a unit area of tissue at the delivery site and, hence, may be independent of the conduit or cannula applied. Thus, the specific tissue resistance may reflect purely a property of the tissue and, therefore, may be advantageously used when this tissue property is assessed in different subjects using different conduit or cannula sizes and when results from this assessment should be compared between the subjects. The specific tissue resistance may also be calculated from the tissue resistance and the cross-sectional area of the conduit end or cannula end as $STR = TR \cdot A$.

In particular, if the pressure is continuously recorded during the first and second measurement, then the tissue resistance (in $kPa \cdot s \cdot mm^{-3}$) may be derived by first calculating the difference between the area under pressure curve obtained during the first measurement ($AUC_{Tissue+System}$; in $kPa \cdot s$) and that obtained during second measurement ($AUC_{System}$; in $kPa \cdot s$), and then dividing the obtained difference by the amount of liquid infused during the first and second measurement (in $mm^3$).

Alternatively or additionally, indirect methods may be applied to derive parameters which strongly correlate with the tissue resistance and specific tissue resistance. For example, from the pressure curve obtained during the first measurement, the times (t; in s) for the pressure to decay to 10%, 25%, 33%, 50%, 66%, 75%, and/or 90% of its maximal value (e.g.: $t_{10\%}$, $t_{25\%}$, $t_{33\%}$, $t_{50\%}$, $t_{66\%}$, $t_{75\%}$, $t_{90\%}$) may be calculated. These times (e.g.: $t_{10\%}$, $t_{25\%}$, $t_{33\%}$, $t_{50\%}$, $t_{66\%}$, $t_{75\%}$, $t_{90\%}$) may be considered to correlate (or be even proportional) with the tissue resistance.

Alternatively or additionally, exponential functions may be applied to fit the time course of the pressure decline observed during the first measurement. The fitted parameters of these exponential functions (e.g., the slopes of the exponential components; k; in $s^{-1}$) may strongly correlate with the tissue resistance and specific tissue resistance. Thereby, the controller may be adapted to adjust one or more of the exogenous factors based on the parameter values obtained by applying these indirect methods.

According to an embodiment of the present invention the arrangement is adapted to adjust (controllable) exogenous factors, in particular the bolus length (total administration duration), for a changing tissue resistance, in order to achieve the predetermined absorption rate of the substance. For example, when it is observed that the tissue resistance is high a shorter bolus length may be required, in order to achieve the predetermined absorption rate of the substance, whereas in the case of a lower tissue resistance, a longer bolus length may be sufficient to achieve the predetermined absorption rate of the substance.

Thereby, a variability of the absorption rate of the substance, in particular insulin, may be reduced. Thereby, an effect of the substance in the organism, in particular the action of insulin on the glucose uptake and glucose production in the organism, may be more accurately predictable.

It has been observed by the inventors that the tissue resistance may decrease during the first 2 to 4 days of administration site use but may steadily increase as the use of the administration site continuous. Because there may be an inverse dependence of the absorption rate on the tissue resistance, the observed time course of the tissue resistance may indicate that the substance absorption rate gradually increases during the first 2 to 4 days of administration site use and then steadily decreases during the subsequent days of its usage. Thus, during prolonged use of the administration site, the tissue resistance may exceed a threshold value, above which adjustments in the bolus length, pulse duration, pulse height, pulse frequency and pulse shape may not be sufficient anymore to achieve a desired absorption rate of the substance. Therefore, once this threshold (tissue resistance threshold) has been reached for a particular administration site, the controller may be adapted to inform the user that the maximum duration of use of the administration site has been reached and that the location of the administration site and conduit should be changed in order to achieve the desired substance absorption rate again.

According to an embodiment of the present invention a relationship between the absorption rate of the substance and the tissue resistance has been previously characterized and mathematically described in a group of individuals as a function of a set of covariates, wherein the set of covariates may include controllable exogenous factors (also referred to as extrinsic covariates), like concentration of the substance in the fluid, bolus length, as well as pulse shape and pulse repetition frequency employed during the bolus delivery. Thus, for each measured tissue resistance value and for a chosen set of covariate values, the corresponding absorption rate of the administered substance may be estimated using the derived relationship between absorption rate and tissue resistance. In particular, to account for possible inter-individual variability in the relationship between absorption rate and tissue resistance, additional intrinsic covariates, like gender, age, weight, height, body-mass-index, body-surface area, and skinfold thickness may be included in the specification of the functional dependence of the absorption rate on the tissue resistance. Due to the inclusion of additional intrinsic covariates, the derived relationship between absorption rate and tissue resistance may also be used to reliably predict absorption rates in individuals who are not members of the group for which the relationship between absorption rate and tissue resistance had been derived previously. In general, for given values of the covariates, there may be an inverse dependence of the absorption rate on the tissue resistance. Thus, the absorption rate may be relatively large at low tissue resistances and may decrease as the tissue resistance increases. Furthermore, if for a measured tissue resistance value and the chosen setting of the controllable exogenous factors, the predicted absorption rate does not equal the predetermined absorption rate, then one or more controllable exogenous factors, like the bolus length, may be appropriately adjusted in order to obtain the desired or predetermined absorption rate of the substance at the administration site. In particular, the bolus length with which the substance-containing fluid is administered may be increased, if the predicted absorption rate is less than the predetermined absorption rate, whereas the bolus length may be increased, if the predicted absorption rate is higher than the predetermined absorption rate.

According to an embodiment of the present invention the absorption rate of the substance has been determined previously in the group of individuals by the measurement of the change in the blood substance concentration following substance administration (appearance studies), by the measurement of the time course of the metabolic effect of the substance following its administration, and/or by labeling the substance with a γ-emitting isotope and measuring changes in the radioactivity at the administration site of the substance (disappearance studies). To assess the effect of (controllable) exogenous factors on the substance absorption, the measurements have been carried out after substance administrations using different settings of the exogenous factors (e.g., with bolus lengths of 0.5 and 10 min).

In the case of the measurement of the change in the blood substance concentration following substance administration, the concentration measurements may be performed frequently (e.g., between 10 and 1000 time) over particular periods of time, in order to derive a change of the concentration of the substance in dependence of the time. Then, by taking into account the substance clearance from the blood and the possible endogenous secretion of the substance, the absorption rate may be derived from the observed substance concentration time courses. Parallel thereto measurements of the tissue resistance (in particular pressure) may be carried out and may be associated to the concentration measurements, thereby enabling to derive the relationship between absorption (rate) and tissue resistance. Substance clearance from the blood may be evaluated independently of the absorption by studying the blood concentration-time courses of the substance administered intravenously. Further, the problem of endogenous substance secretion may be circumvented either by studying individuals lacking the endogenous substance secretion (e.g., C-peptide negative patients in the case of diabetes), or by using analogues of the substance which are not produced in the organism (e.g., rapid-acting analogues in the case of insulin).

Further, in the case of the measurement of the metabolic effect of the substance, the obtained time course of this effect may be related to the absorption rate of the substance. In particular, if the administered substance is insulin, then the time course of the action of insulin on the glucose uptake and glucose production, reflected as changes of the glucose concentration in the blood, may be indicative of the insulin absorption rate. Furthermore, to avoid hypoglycemic events following insulin administration, glucose may be intravenously infused at a variable rate, in order to keep the blood glucose concentration at a constant level. The obtained time course of the infusion rate of the glucose may thus represent the time course of the metabolic effect of the administered insulin. In addition, hypoglycemic events may also be avoided, when after the administration of insulin, carbohydrates are ingested in the form of a standard glucose load or a standard meal. The observed blood glucose excursions following insulin administration and carbohydrate ingestion may then be indicative of the time course of insulin's metabolic effect.

In general, using both the measurement of the change in the blood substance concentration and the measurement of the time course of the metabolic effect of the substance, a complete picture of the absorption process of the substance may be obtained and, if combined with the measurement of the tissue resistance, an accurate relationship between the absorption rate and the tissue resistance may be derived.

According to an embodiment of the present invention the controller is adapted to control one or more of the exogenous factors (e.g., bolus length) further based on the usage time of the administration site and inserted conduit, in particular usage time of the cannula.

It has been observed by the inventors that during the first 2 to 4 days of infusion site usage, the tissue resistance decreases, such that a bolus delivery with a long bolus duration (e.g., 10 min) is sufficient to achieve a baseline absorption rate of the substance. The baseline absorption rate of the substance is observed when a bolus delivery of the substance is performed immediately after conduit insertion using a short bolus length (e.g., 0.5 min). Thus, taking into account the changing tissue resistance during the wear time of the inserted conduit may advantageously allow to accurately adjust the exogenous factors, in order to achieve the predetermined (e.g. desired or intended) absorption rate of the substance.

According to an embodiment of the present invention the member comprises a storage medium storing the information, the information being based on at least one previous measurement of the tissue resistance, in particular in dependence of a set of covariates, wherein the set of covariates may include a wear time of the inserted conduit, duration of use of the administration site, type of tissue in which the conduit is inserted, insertion region within the tissue, conduit insertion depth, time of day, gender, age, weight, height, body-mass-index, body-surface area, and/or skinfold thickness. Then, obtaining the information comprises:

accessing the information in the storage medium.

The member may comprise a pressure sensor and a storage medium or only a storage medium and no pressure sensor. When the member comprises the pressure sensor and the storage medium, the arrangement, in particular the member may be adapted to also store measurement values acquired by the pressure sensor. In particular, the measurement values may be acquired over time when a pressure difference may be computed over time.

Further, a relationship between the tissue resistance and a set of covariates may have been previously characterized and mathematically described in a group of individuals, wherein the set of covariates may include a wear time of the inserted conduit, type of tissue in which the conduit is inserted, insertion region within the tissue, conduit insertion depth, duration of use of the infusion site, time of day, gender, age, weight, height, body-mass-index, body-surface area, skinfold thickness, skin temperature, and/or tissue blood flow. Thus, for a chosen set of covariate values, the corresponding tissue resistance may be estimated using the derived relationship between tissue resistance and covariates. Due to the inclusion of intrinsic covariates, like gender, age, weight, and height, the derived relationship between tissue resistance and covariates may also be used to reliably predict the tissue resistance in individuals who are not members of the group for which the relationship had been derived previously. Thus, in the case of an existing relationship between the tissue resistance and a set of covariates, obtaining the information comprises: Choosing the setting of the covariates by the user and accessing the information in the storage medium based on the chosen covariate settings. Thereby, the arrangement may not require a pressure sensor to measure the actual pressure or pressure difference. Thereby, the arrangement may be simplified.

According to an embodiment of the present invention the substance comprises insulin (in particular as a solute) and the liquid is an aqueous solution (thus the solvent being water and possibly additional salt(s)), wherein in particular the conduit is adapted to be inserted at the one end into the cutaneous tissue or the subcutaneous tissue of a human.

According to an embodiment of the present invention the arrangement for administering a predetermined amount of a substance into an organism is used for administering insulin into a human.

It should be understood that features which are individually or in any combination described, explained or mentioned in the context of an arrangement for administering a predetermined amount of a substance into an organism may also be applied (individually or in any combination) to any embodiment of a method of administering a predetermined amount of a substance into an organism according to an embodiment of the present invention and vice versa.

According to an embodiment of the present invention it is provided a method of administering a predetermined amount of a substance into an organism, the method comprising: providing information indicative of a tissue resistance against flow of a fluid containing the substance upon administration into the tissue; controlling a flow rate of the fluid based on the information such as to achieve a predetermined absorption rate of the substance.

According to an embodiment of the present invention the method is performed at times when the blood glucose concentration is higher than the target level as well as during, after, or in a time interval of 1 second to 30 minutes before ingestion of a meal. Thereby, appropriate insulin infusion in order to efficiently normalize the blood glucose concentration when the glucose level is in the hyperglycemic range and to maintain normal glucose levels after ingestion of carbohydrate-containing meals, may be realized.

In the following, particular embodiments of the present invention will be described with reference to the accompanying drawings. However, the invention is not limited to the described or illustrated embodiments.

DETAILED DESCRIPTION OF ILLUSTRATED EMBODIMENTS

Figure 1:
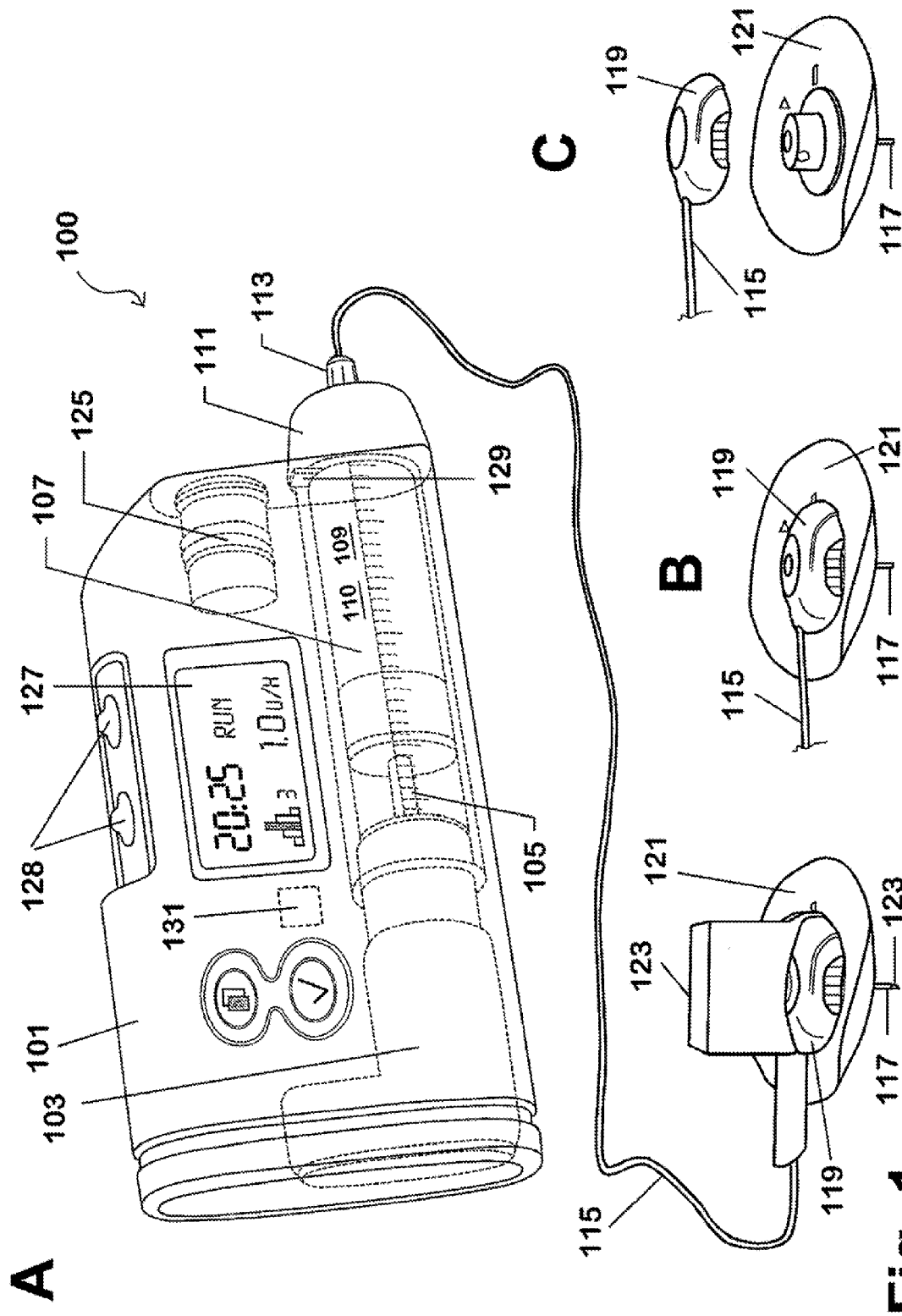
FIGS. 1A, 1B, 1C schematically illustrate an arrangement for administering a substance into an organism according to an embodiment of the present invention.

FIGS. 1A, 1B and 1C schematically illustrate an arrangement 100 for administering a substance into a not illustrated organism according to an embodiment of the present invention. The arrangement 100 comprises a casing 101 in which a driving portion or pump 103, using e.g. an electric motor, is harbored which drives a piston 105 to affect a size of a reservoir 107 in which a liquid 109 (containing the substance 110, in this case insulin) is contained and thus to pump the solution or liquid 109. The reservoir 107 comprises a reservoir cap 111, at which a connector 113 is connected connecting the reservoir 107 to a tubing 115, which allows the liquid 109 to be conveyed to a cannula 117 which is insertable into a tissue of a human. Thereby, the tubing 115 comprises a tubing connector 119 which allows to remove the cannula 117. Thereby the tape 121 enables to fix the tubing connector harboring the cannula 117 at a skin of the human.

For sake of clarity, the cannula 117 is illustrated in three configurations, namely together with insertion needle 123 and connected tubing 115 (see FIG. 1A), without insertion needle 123 and with connected tubing 115 (FIG. 1B) and without insertion needle 123 and without connected tubing 115 (FIG. 1C).

The arrangement 100 further comprises a battery 125 for powering the motor 103 and also powering the display 127 at which for example the flow rate of the insulin solution 109 (the liquid) expelled from the reservoir is displayed.

For measuring a pressure within the reservoir 107 the arrangement 100 comprises a pressure sensor 129 which in the illustrated embodiment is arranged within the reservoir cap 111 to measure the pressure within the reservoir 109 and thus also (indirectly) the pressure in the tubing 115. The pressure sensor 129 may in other embodiments located at different places, such as at the motor assembly 103, in the reservoir assembly 107 or in the infusion line assembly comprising the tubing 115, cannula connector 119 and the cannula 117. In all cases, however, the pressure sensor 129 is adapted to measure a pressure of the insulin liquid or any other liquid contained within the reservoir 107 or to measure the pressure at any location between the reservoir 107 and the end of the cannula 117.

The arrangement 100 further comprises within the casing 101 a controller 131 which receive pressure measurement data from the pressure sensor 129 and is adapted to control the motor 103, in order to adjust a flow rate of the liquid 109 contained within the reservoir 107 based on the pressure measurement data.

Figure 2:
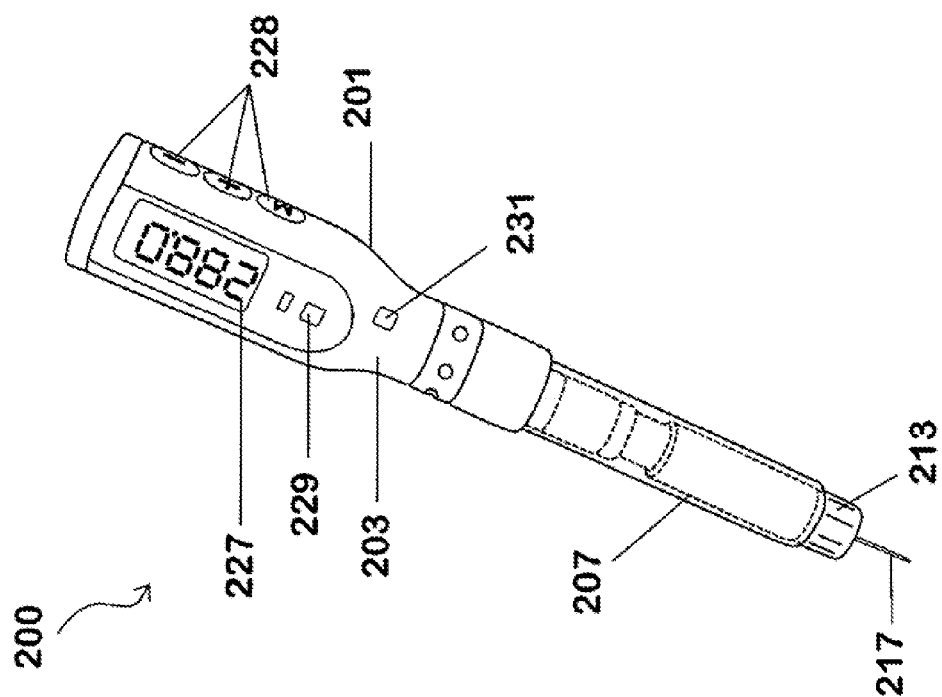
FIG. 2 illustrates in a schematic form an arrangement for administering a predetermined amount of a substance into an organism according to another embodiment of the present invention.

FIG. 2 illustrates another embodiment 200 of an arrangement for administering a substance into an organism, here embodied as a pen-like administration device. The device comprises a casing 201 which harbors a not illustrated driving assembly 203, a display 227, operation bottoms 228, a reservoir 207 and a sharp-tipped, metallic cannula 217 which is insertable into a tissue of a human. In the illustrated embodiment the pressure sensor 229 is located at or close to the driving assembly 203. Alternatively, the pressure sensor 229 may be located at the reservoir assembly 207. Further, the controller 231 is harbored in the casing 201 of the arrangement 200. Connector 213 connects the cannula 217 to the casing 201.

FIGS. 3A, 3B, 3C, 3D schematically illustrate a usage of an arrangement 300 (illustrated in FIGS. 3A, 3B) according to an embodiment of the present invention. The arrangement 300 comprises a casing 301 comprising a display 327 and harboring a not illustrated motor unit, a controller, a battery and a reservoir. At an exit portion or connector portion 313 a pressure sensor 329 is connected to be in communication with the insulin solution (contained in the reservoir) which is then further conveyed through the tubing 315 to a cannula 317 which is, however, illustrated in FIG. 3C. The arrangement 300 comprises the controller 331 in the form of a computer which is programmed to perform the control functions, such as to control the flow rate of a motor drive contained within the casing 301.

Figure 3:
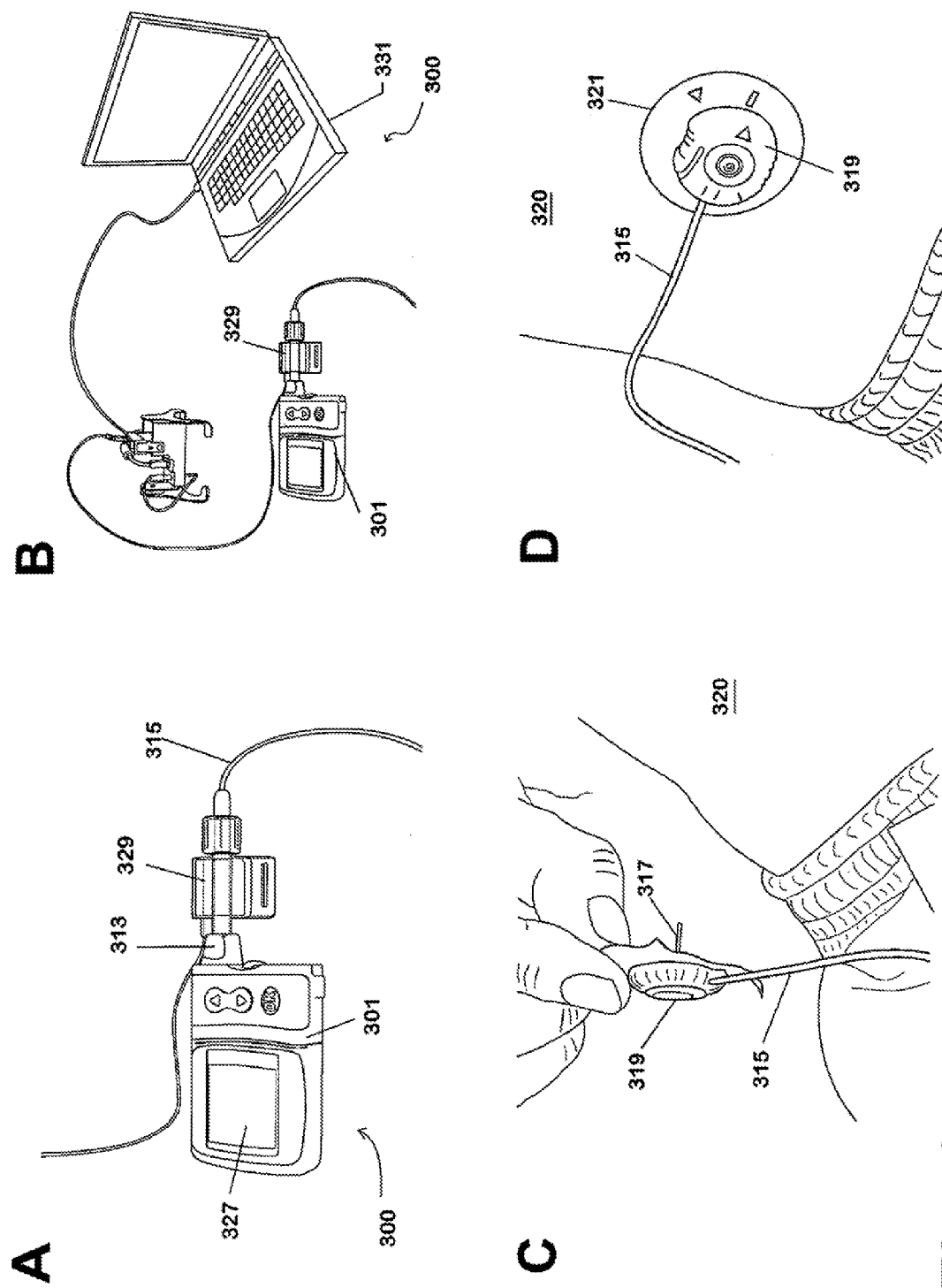
FIGS. 3A, 3B, 3C, 3D schematically illustrate a usage of an arrangement for administering a substance into an organism according to a further embodiment of the present invention.

According to a usage of the arrangement 300 in FIG. 3, or the arrangement 100 illustrated in FIG. 1, or the arrangement 200 illustrated in FIG. 2, the motor drive or electric pump is set to a particular power or flow rate, while the cannula 317 is not yet inserted into the tissue of the organism but is held at atmospheric pressure, as is illustrated in FIG. 3C. In this situation, while the flow rate is adjusted to a defined value, the pressure within the reservoir or the tubing (such as tubing 315, or reservoir 107, or reservoir 207) is measured, in order to obtain a pressure related to the system resistance (system reference measurement) generated by the resistance of the system components of the arrangement for administering the substance, such as the reservoir, the pressure sensor and the tubing, as well as the resistance associated with flow of the liquid through the cannula 317. Thus, in particular, in a situation as illustrated in FIG. 3C a second pressure measurement is performed, wherein one end of the cannula is external to the tissue 320.

After performing the second pressure measurement, the cannula 317 is inserted into the tissue 320 and is fixed using the tape 321 at the skin covering the tissue, as is illustrated in FIG. 3D. In this situation, the flow rate of the liquid conveyed through the tubing 315 is set to the value previously used, while the cannula 317 was external to the tissue, and the pressure inside the tubing or inside the reservoir is again measured using the pressure sensor 329 illustrated in FIG. 3A.

FIGS. 4A, 4B and 4C illustrate measurement results of performing the second pressure measurement, when one end of the cannula is external to the tissue and the first pressure measurement, when the one end of the cannula is inserted into the tissue 320 of a healthy subject.

During performing the measurements illustrated in FIGS. 4A, 4B and 4C a saline solution was pumped into the cannula, wherein FIG. 4A illustrates the measurement values when the pressure was measured immediately after insertion of the cannula 317, the FIG. 4B illustrates the situation, wherein the pressure measurements were performed 24 hours after inserting the cannula 317 and the measurement values illustrated in FIG. 4C were acquired 48 hours after inserting the cannula 317 into the tissue 320.

In particular, FIG. 4A illustrates as measurement points 435 the pressure values as obtained during the second pressure measurement, when the cannula 317 is external to the tissue 320 and further illustrates measurement values 437 which were obtained, while the cannula 317 was inserted into the tissue 320. The measurement values 439 in FIG. 4B denote the pressure values, while the cannula was external to the tissue 320, while the measurement values 441 illustrate the measurement values of the pressure, while the cannula 317 was inserted into the tissue. Further, the measurement values 443 of FIG. 4C illustrate the pressure values obtained, when the cannula 317 was external to the tissue 320, while the measurement values 445 illustrate the pressure measurement data, while the cannula 317 was inserted into the tissue 320.

Figure 4:
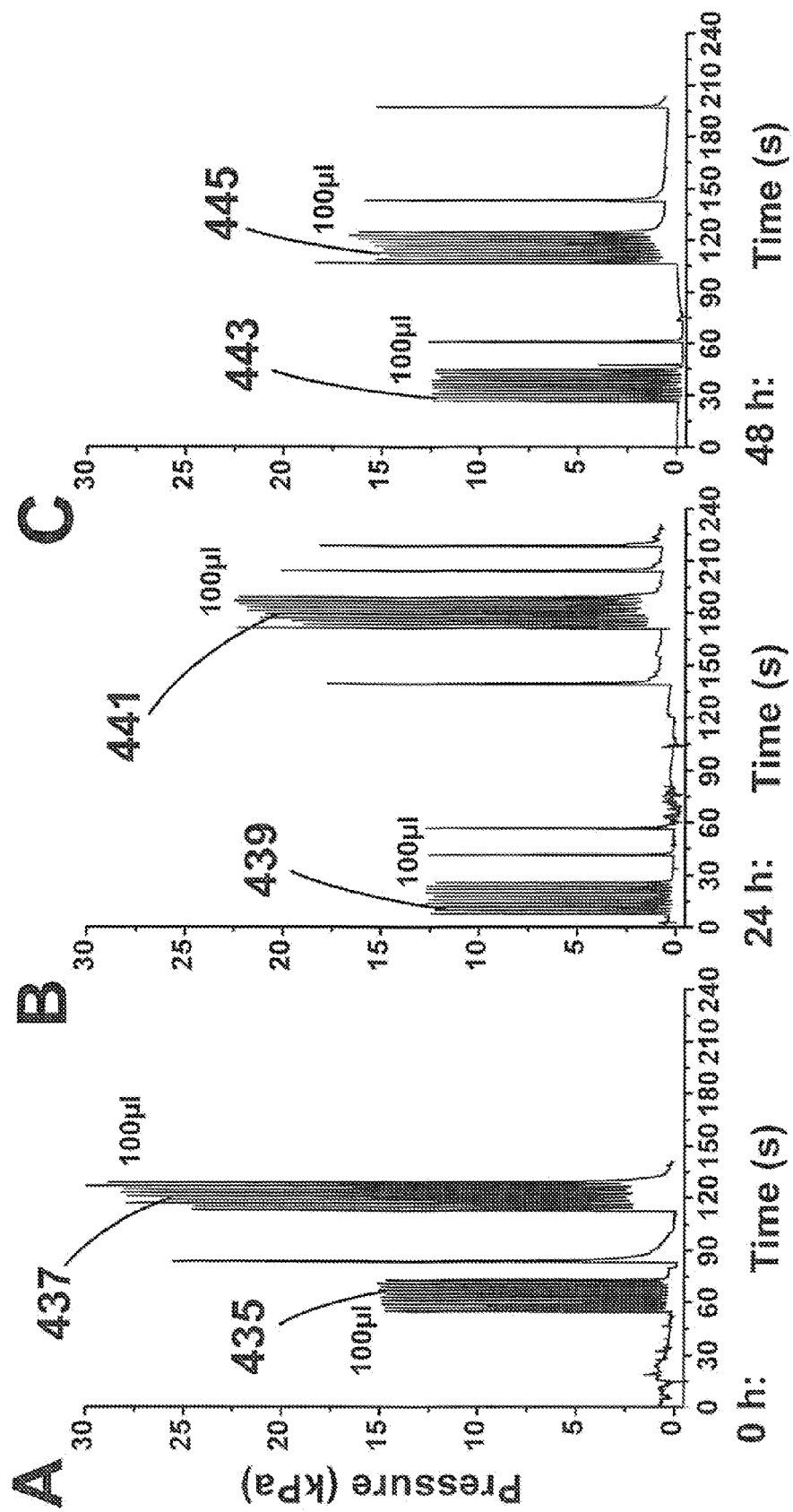
FIGS. 4A, 4B, 4C illustrate results of pressure measurements performed in a healthy subject by one of the arrangements illustrated in FIG. 1, 2 or 3 according to an embodiment of the present invention.

As can be appreciated from FIGS. 4A, 4B and 4C the pressure is higher in every case, when the cannula 317 is inserted into the tissue (measurement points 437, 441, 445) compared to the situation when the cannula 317 is not inserted into the tissue (measurement points 435, 439, 443). Further, it can be appreciated from FIG. 4 that the longer the wear time of the cannula 317 the smaller is the pressure when the cannula 317 is inserted into the tissue.

Figure 5:
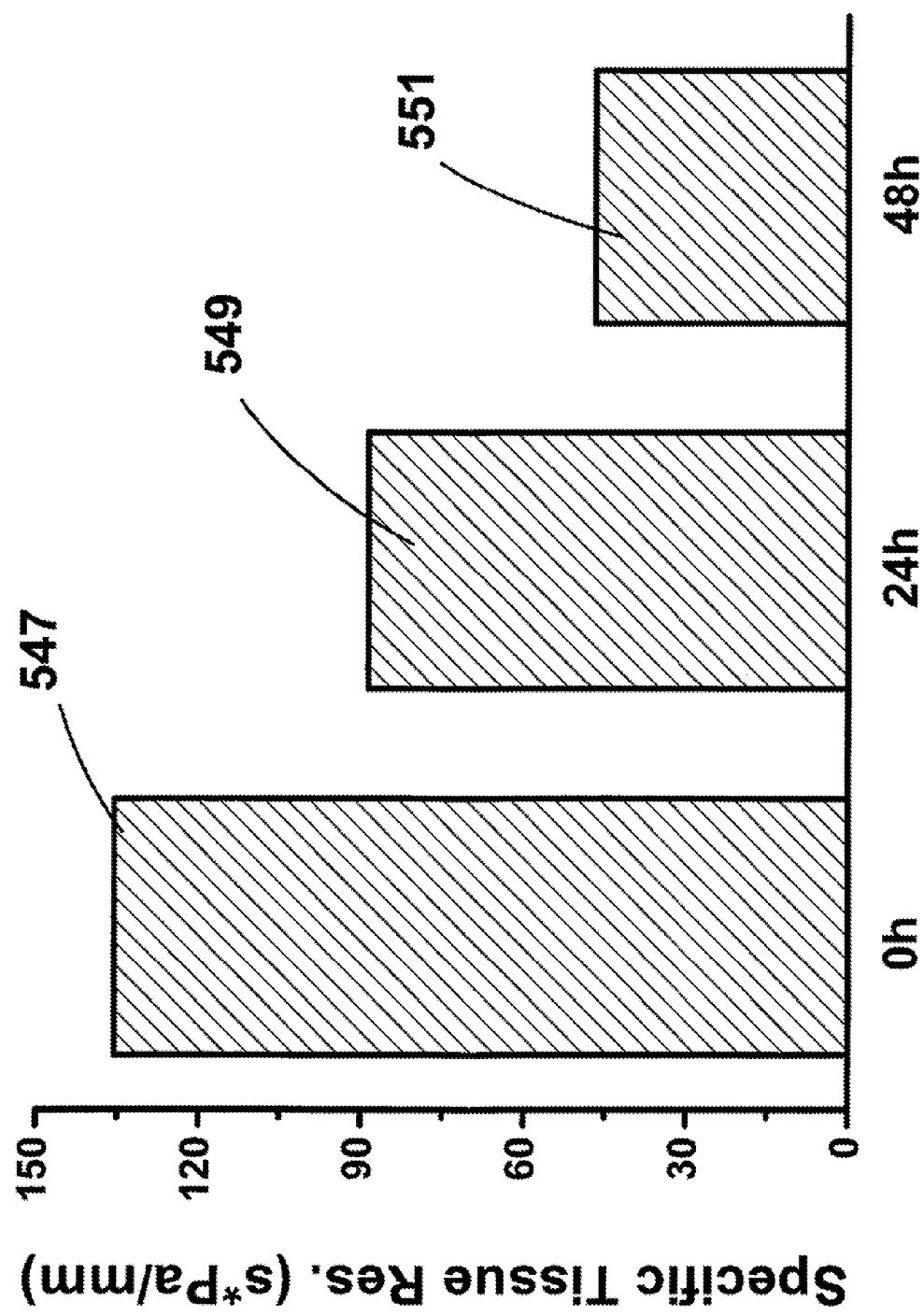
FIG. 5 illustrates specific tissue resistance values of a healthy subject measured with one of the arrangements illustrated in FIG. 1, 2 or 3 according to an embodiment of the present invention.

FIG. 5 illustrates specific tissue resistances (columns 547, 549 and 551) calculated from the observed differences of the pairs of pressure values (437, 435); (441, 439) and (445, 443), applied flow rates, and the cross-sectional area of the used cannula 317. In particular, the column 547 illustrates the specific tissue resistance measured immediately after inserting the cannula 317 into the tissue, whereas the columns 549 and 551 depict the specific tissue resistances measured 24 and 48 hours after inserting the cannula 317 into the tissue 320, respectively. As can be appreciated from FIG. 5 the tissue resistance increases with increasing wear time of the cannula 317.

In particular, the pressure changes monitored during the saline infusion may be generated by a combined resistance of the infusion line, e.g. the tubing 315 (i.e. hydraulic resistance from pumping the solution through a tube with small diameter) and the resistance evolving from the tissue 320 into which the cannula 317 is inserted. To separate and quantitate the pressure induced by the infusion line and that induced by the tissue, the pressure generated by pumping the saline solution through the infusion line alone is monitored prior to the saline infusion into the tissue (points 435, 439, 443 in FIG. 4). In particular, the tissue resistance (in Pa·s·mm$^{-3}$) was derived by calculating differences between the area under pressure curve obtained during the infusion of 90 µl of saline solution into the tissue ($AUC_{Tissue+System}$; in Pa·s) and that obtained during the infusion of 90 µl of saline solution through the infusion line alone ($AUC_{System}$; in Pa·s), and by dividing the obtained difference by the infused amount of liquid (i.e., 90 mm$^3$). The specific tissue resistance (in Pa·s·mm$^{-1}$) was then calculated by multiplying the tissue resistance value by the cross-sectional area of the used cannula (i.e., 0.113 mm$^2$).

Parallel to monitoring the pressure difference the insulin absorption rate and/or insulin action may be monitored in a clinical study in order to derive an exact relationship between the tissue resistance and the insulin absorption rate or insulin action.

FIGS. 6A, 6B shows on its abscissas 663 and 664 the time and on an ordinate 665 the plasma concentration of a rapid-acting insulin analogue (aspart) and on an ordinate 666 the glucose infusion rate (GIR), which has been applied in order to keep the glucose concentration constant. FIG. 6A shows the mean time courses of the plasma insulin concentration for healthy subjects (n=10) after an administration of 0.1 U/kg of the rapid-acting insulin on day 0 and 4 after cannula insertion. In FIG. 6B, mean glucose infusion rate profiles for diabetic subjects (n=17) on day 1 versus day 4 of cannula site use are depicted. These insulin action profiles were observed after the administration of 0.2 U/kg of rapid-acting insulin analogues. FIGS. 6A and 6B were redrawn from the original figures published in Clausen T S et al., Diabetes Techn. & Ther. 2009, 11(9):575-580 and Swan K L et al., Diabetes Care 2009, 32(2):240-244, respectively.

Figure 6:
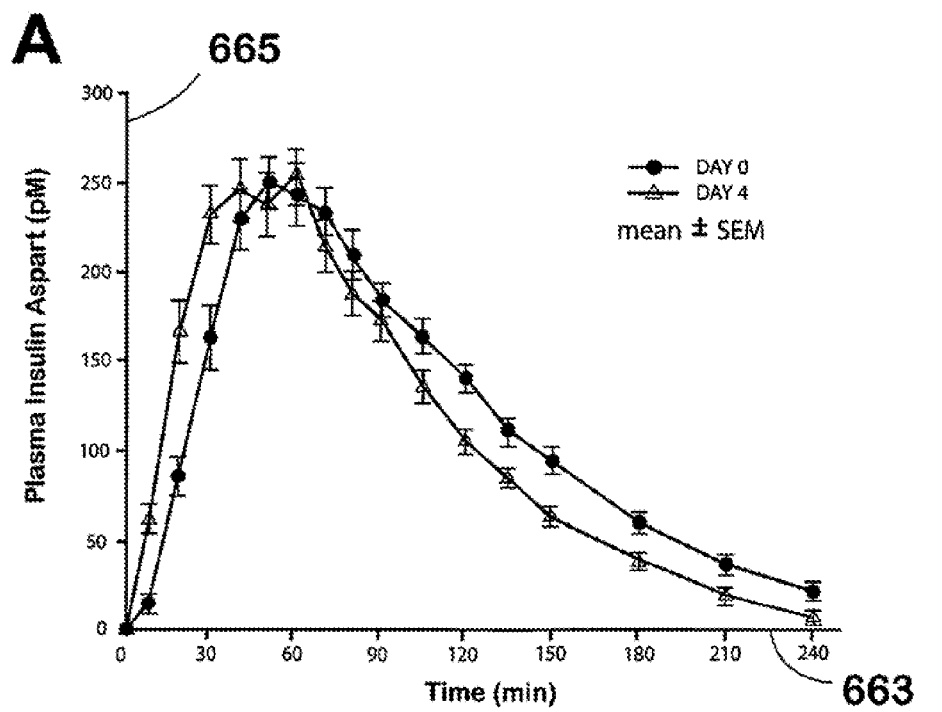
FIGS. 6A, 6B illustrate data indicative of an absorption rate of insulin or an action of insulin.
Figure 6:
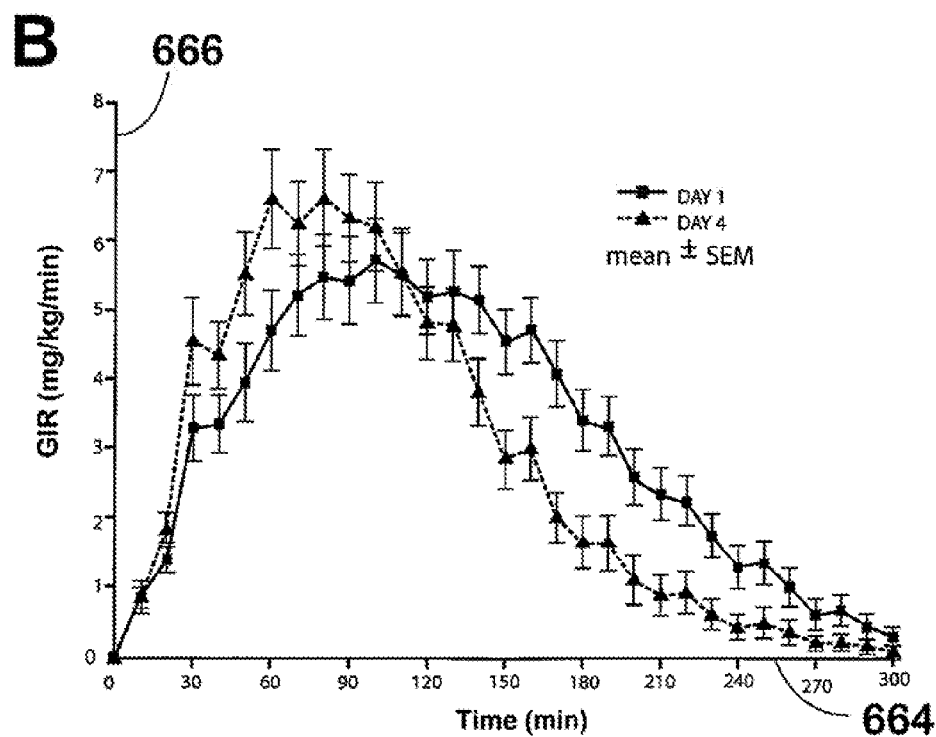
Figure 8:
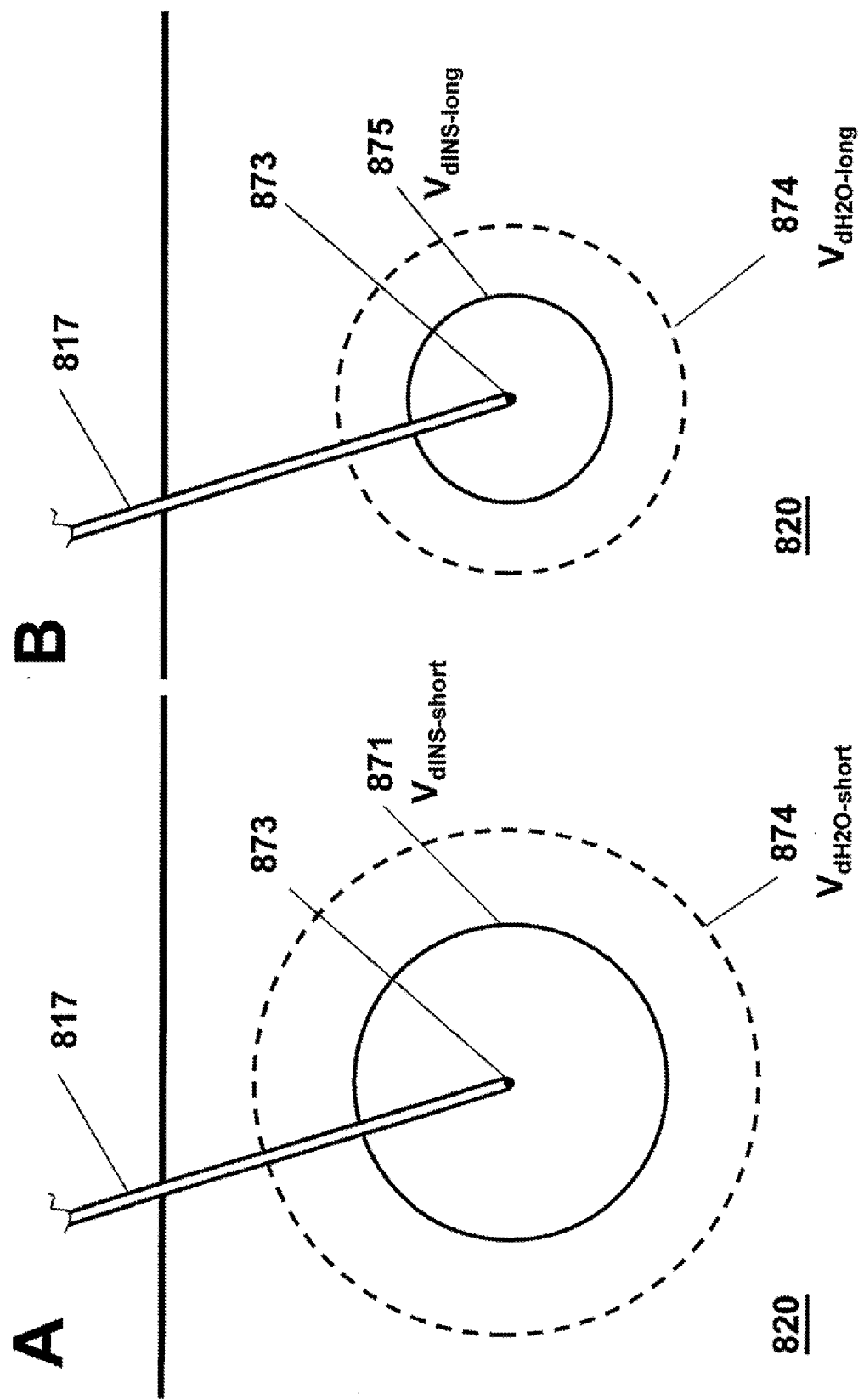
FIGS. 8A, 8B illustrate distribution volumes of insulin modeled according to usage of the arrangement illustrated in FIG. 1, 2 or 3 according to an embodiment of the present invention.

In particular, the time courses of the plasma insulin concentration and the glucose infusion rate depicted in FIG. 6 show that a more prolonged use of an infusion site results in a faster appearance of insulin in the blood (see FIG. 6A) and in an earlier peak insulin action (see FIG. 6B) following a standard bolus dose. Further, comparison of these findings with the observation of decreasing tissue resistance with increasing cannula wear time (FIGS. 4 and 5) strongly suggests that there is an inverse dependence of the absorption rate on the tissue resistance. Thus, the absorption rate may be relatively large at low tissue resistances and may decrease as the tissue resistance increases. In fact, the decreasing tissue resistance may cause increasing insulin distribution volumes following insulin bolus administrations which in turn may expose a higher number of capillaries to insulin, thereby increasing the absorption of insulin (see also FIG. 8). Thus, a strong relationship between tissue resistance and the insulin absorption following bolus administrations of insulin is suggested. Thereby, the tissue resistance may be an easily measurable parameter using a pressure sensor, from which the speed of insulin absorption, or the insulin absorption rate may be estimated.

Figure 7:
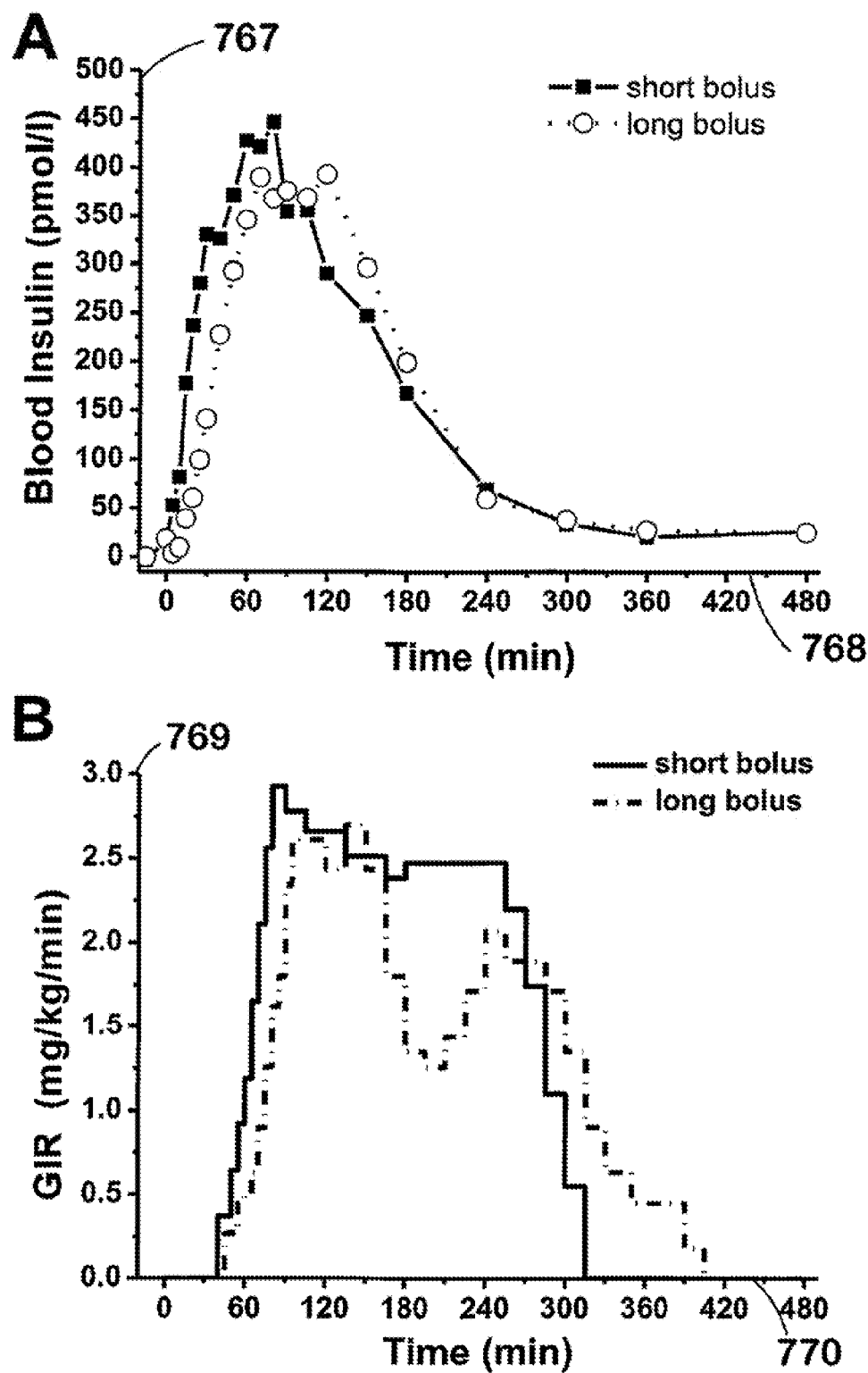
FIGS. 7A, 7B illustrate data of insulin concentration and glucose infusion rate related to usage of the arrangement illustrated in FIGS. 1, 2 and 3.

FIGS. 7A, 7B depict measurement data of blood concentration of a rapid-acting insulin analogue (ordinate 767 in FIG. 7A) and glucose infusion rate (ordinate 769 in FIG. 7B) over time (abscissas 768 and 770 in FIGS. 7A and 7B). In particular, FIG. 7 shows representative measurement data obtained from a study evaluating the pharmacodynamics and pharmacokinetics of rapid-acting insulin lispro administered as subcutaneous boluses with different bolus durations. The study was performed in 20 type 1 diabetic subjects having no residual endogenous insulin secretion (C-peptide negative). The subjects came to the clinical research center for two study visits. On the first study day, subjects were randomized to receive a subcutaneous insulin bolus with a short or long bolus duration. On the second study day the subjects received the subcutaneous insulin bolus with the alternate bolus duration. Subjects fasted overnight before each study visit.

On each study day, a new infusion cannula was inserted and, immediately after cannula insertion, an insulin bolus (15 U Lispro, Eli-Lilly; =150 µl of liquid) was administered over a period of 0.5 minutes (short bolus duration) or 10 minutes (long bolus duration). For the delivery of the bolus with short duration (infusion rate=300 µl/min), a pump from Animas (OneTouch Ping Insulin Pump) was used, whereas for the insulin delivery with long bolus duration (infusion rate=15 µl/min) a pump from Medtronic Minimed (Paradigm 722 Insulin Pump) was used. The type of infusion cannula used in the study was the same for both visits. To maintain euglycemia after each insulin bolus administration, glucose was infused intravenously at a variable rate. The adjustments in the glucose infusion rate were based on the arterialized plasma glucose concentrations measured frequently at the bedside (euglycemic clamp technique). To ensure the arterialization of the frequently drawn blood samples, the forearm with the sampling catheter was placed under a heating blanket (50° C.) during the study.

On the average, intravenous glucose infusion was started 13.3 minutes earlier for bolus administration with short bolus duration than in the case of bolus administration with long bolus durationt ($t_{GIRstart}$: 21.0±2.5 vs. 34.3±2.7 min; p<0.002). In addition, time to reach maximum insulin effect ($t_{GIRmax}$) was found to be 27 minutes earlier for bolus administration with short bolus duration compared to that with long bolus duration (98±11 min vs. 125±16 min; p<0.005). However, the maximum glucose infusion rate ($GIR_{max}$) was similar in both bolus administration methods (6.2±0.8 vs. 5.5±0.7 mg/kg/min for short vs. long bolus duration). Furthermore, average insulin concentration in blood plasma rose to a peak of 345±33 pmol/l by 75.0±5.2 min after the insulin administration with short bolus duration, and to a peak of 333±23 pmol/l by 86.0±6.8 min after administration with long bolus duration. The incremental area under the plasma insulin curve from 0 to 60 min was ~20% higher for the bolus administration with short bolus duration than for that with long bolus duration ($AUC_{INS\ 0-60\ min}$: 10307±1291 vs. 8192±865 min·pmol/l, p=0.027).

Thus, these derived pharmacokinetic and pharmacodynamic parameters and the data illustrated in FIGS. 7A and 7B suggest that a bolus administration using a short bolus duration results in a faster insulin absorption rate and a faster insulin action compared to a bolus administration using a long bolus duration.

FIGS. 8A, 8B illustrate schematically an infusion site 873 and the distribution volume 871 and 875 achieved after a subcutaneous bolus administration of 15 units of insulin using a short (FIG. 8A) and long (FIG. 8B) bolus duration, respectively. Due to the fast absorption of fluid (or solvent) into the blood and the high filtration reflection factor for insulin, the distribution volume 871 of 15 units of insulin (=150 µl of a 100 unit/ml insulin solution) delivered at a high flow rate (e.g., 300 µl/min) for 0.5 min ($V_{dINS-short}$; FIG. 8A) may be substantially larger than the distribution volume 875 of 15 units of insulin delivered at a low flow rate (e.g., 15 µl/min) for 10 min ($V_{dINS-long}$; FIG. 8B). The larger distribution volume 871 (FIG. 8A) may expose a higher number of capillaries to insulin, thereby increasing the absorption of insulin. Differences in the distribution volume of solvent 874 (or $V_{dH2O}$) and the distribution volume of insulin 871 and 875 (or $V_{dINS}$) may be caused by retardation of insulin in the interstitial space.

Similar discrepancies between the distribution volumes may result from administration of bolus amounts of insulin solutions after different usage times of the administration site and cannula. In particular, absorption of insulin into the blood may increase (and also the distribution volume may increase) during the first 2-4 days of administration site and cannula use.

Thus, to reduce or even eliminate the insulin absorption variability associated with the duration of infusion site use, it is suggested to measure the tissue resistance at the infusion site, and then administer the insulin bolus with bolus durations depending on the measured tissue resistance. For example, immediately after cannula insertion, a high tissue resistance will be measured. Hence, for bolus administrations of insulin, a short bolus duration (e.g., 0.5 min) should be applied. In contrast, after longer cannula wear-times (e.g., after 24 hours) a lower tissue resistance will be measured and, hence, for bolus administrations of insulin, a longer bolus duration (e.g., 5 min) should be applied.

FIGS. 9A, 9B, 9C and 9D illustrate, for different time intervals after inserting the cannula into tissue of an organism, measurement results of performing the second pressure measurement, when one end of the cannula is external to the tissue and the first pressure measurement, when the one end of the cannula is inserted into the tissue 320 of a diabetic subject.

During performing the measurements illustrated in FIGS. 9A, 9B, 9C and 9D a rapid-acting insulin solution was pumped into the cannula.

Figure 9:
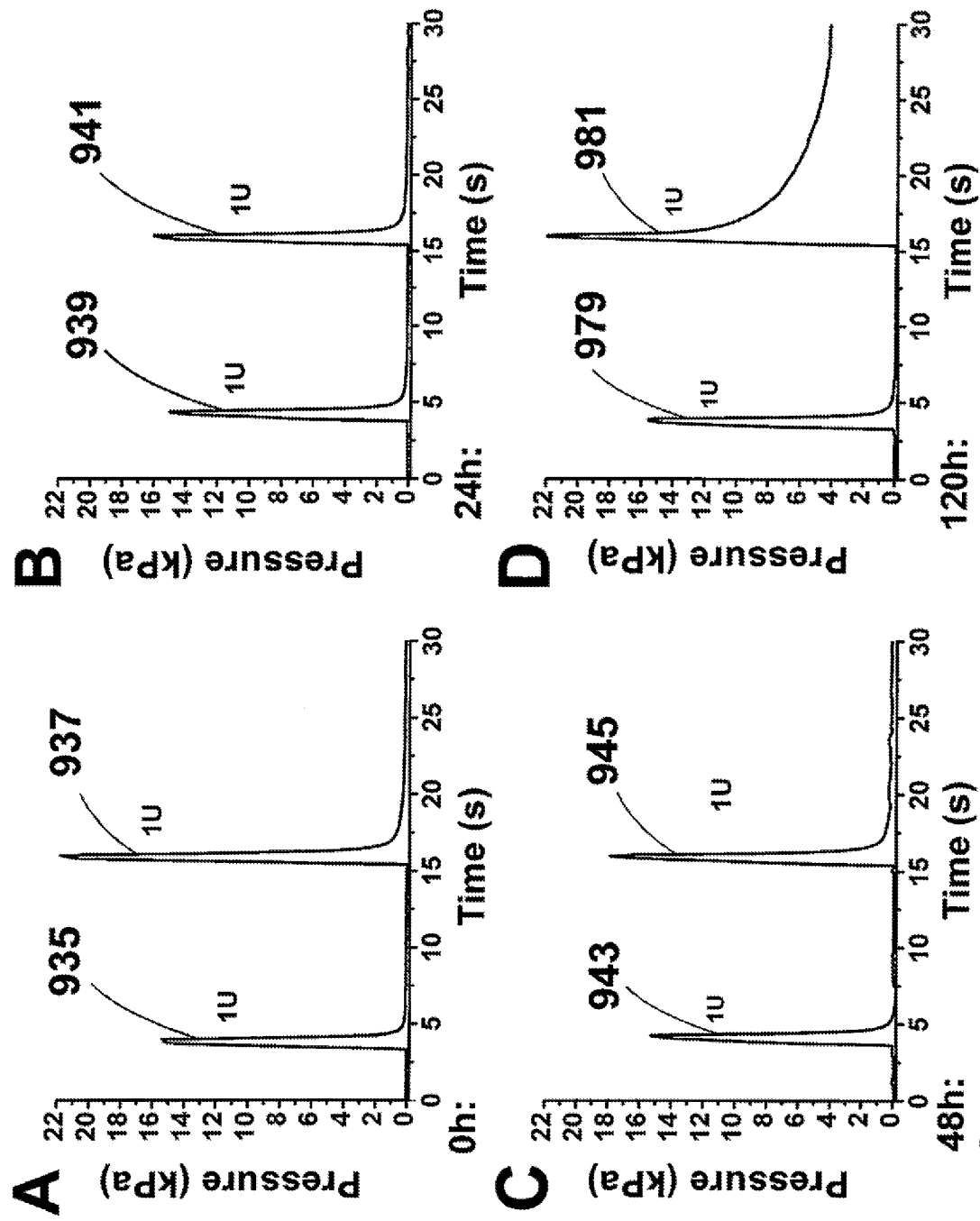
FIGS. 9A, 9B, 9C, 9D illustrate results of pressure measurements performed in a diabetic subject by one of the arrangements illustrated in FIG. 1, 2 or 3 according to an embodiment of the present invention.

In particular, FIGS. 9A, 9B, 9C, 9D illustrate time courses of a pressure, as measured using an arrangement for administering a predetermined amount of a substance into an organism according to an embodiment of the present invention, such as the arrangement as illustrated in FIG. 1, FIG. 2, FIG. 3. In particular, the abscissas in FIGS. 9A to 9D indicate the time and the ordinate indicate the pressure of the fluid which is administered into an organism. Thereby, the measurement results illustrated in FIG. 9A are obtained 0 hours after inserting the cannula, the measurement results illustrated in FIG. 9B have been obtained 24 hours after inserting the cannula, the measurement results illustrated in FIG. 9C are obtained 48 hours after inserting the cannula, and the measurement results illustrated in FIG. 9D have been obtained 120 hours after inserting the cannula into the organism.

Thereby, in FIGS. 9A-9D the curves 935, 939, 943 and 979 represent the pressure time courses when one end of the cannula is external to the tissue of the organism, thus representing a second pressure measurement, and the curves 937, 941, 945 and 981 represent pressure time courses when one end of the cannula is inserted into the tissue of the organism, thus representing first pressure measurements. Thereby, in particular the first pressure measurement and the second pressure measurement may be performed by the arrangements illustrated in FIG. 1, 2 or 3 during a method of administering a substance into an organism. Further, the results of these measurements may be utilized in order to derive information indicative of a tissue resistance against flow of the fluid which is administered to the organism. Furthermore, the tissue resistance information may be used by a controller of the arrangements illustrated in FIG. 1, 2 or 3 to adjust an administration characteristic of the fluid which is administered to the organism. The same holds for the pressure time courses illustrated in FIGS. 11A-11C which will be described below.

Figure 10:
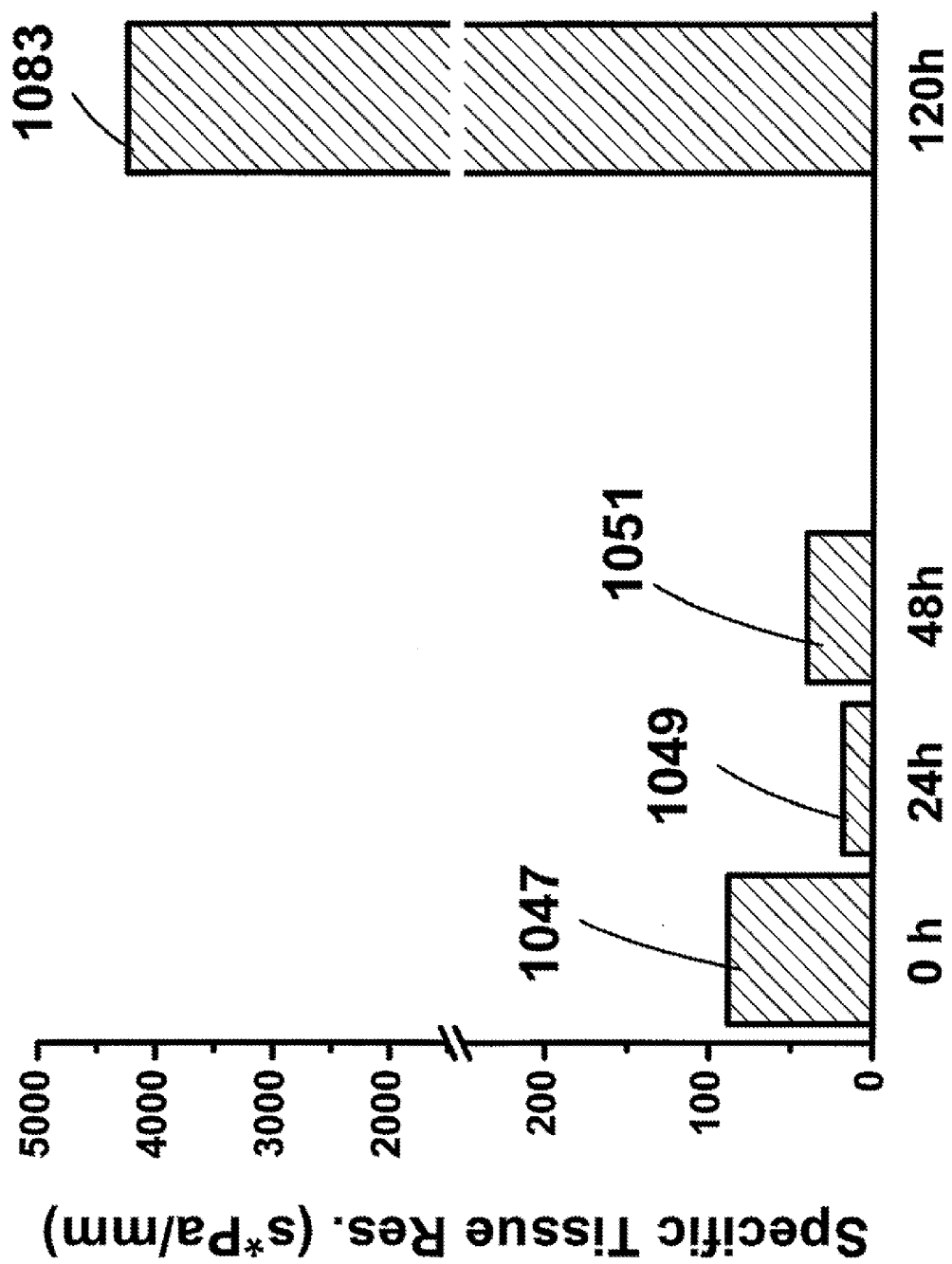
FIG. 10 illustrates specific tissue resistance values of a diabetic subject measured with one of the arrangements illustrated in FIG. 1, 2 or 3 according to an embodiment of the present invention.

FIG. 10 illustrates specific tissue resistances (columns 1047, 1049, 1051 and 1083) calculated from the observed differences of the pairs of pressure values (937, 935); (941, 939); (945, 943) and (981,979) illustrated in FIGS. 9A-9D, applied flow rates, and the cross-sectional area of the used cannula 317.

In particular, FIG. 10 illustrates evaluation results of evaluating the pressure time courses illustrated in FIGS. 9A-9D according to an embodiment of the present invention, which may for example be performed by the arrangement illustrated in FIG. 1, 2 or 3. The columns 1047, 1049, 1051 and 1083 in FIG. 10 illustrate specific tissue resistances associated with the pressure course measurement illustrated in FIGS. 9A, 9B, 9C and 9D, respectively. In particular, to derive column 1047 a difference between the area under the curves 937 and 935 is calculated which is then divided by the amount of fluid administered and which is also divided by the cross-sectional area of the used cannula. As can be appreciated from FIG. 10, the specific tissue resistance varies with the time interval after the cannula has been inserted into the anatomical location of the organism. In particular, the specific tissue resistance 0 hour after inserting the cannula (column 1047) is higher than 24 hours after inserting the cannula (column 1049). Further, the specific tissue resistance (column 1051) 48 hours after insertion of the cannula is higher than 24 hours after inserting the cannula (column 1049). Further, 120 hours after insertion of the cannula, the tissue resistance is strongly increased relative to the tissue resistances observed 0 hours, 24 hours or 48 hours after insertion of the cannula.

According to an embodiment of the present invention a threshold of the tissue resistance may be defined. According to an embodiment, if the specific tissue resistance threshold is exceeded, the arrangement, such as arrangement 1 as is illustrated in FIG. 1, 2 or 3, may indicate that the anatomical location at which the cannula is inserted should be changed and another anatomical location should be chosen where to insert the cannula or even a novel or fresh cannula. It should be noted however, that the pressure time courses illustrated in FIGS. 9A to 9D may be evaluated in a manner different from the manner illustrated in FIG. 10, in order to derive a criterium when the anatomical location should be changed.

Figure 11:
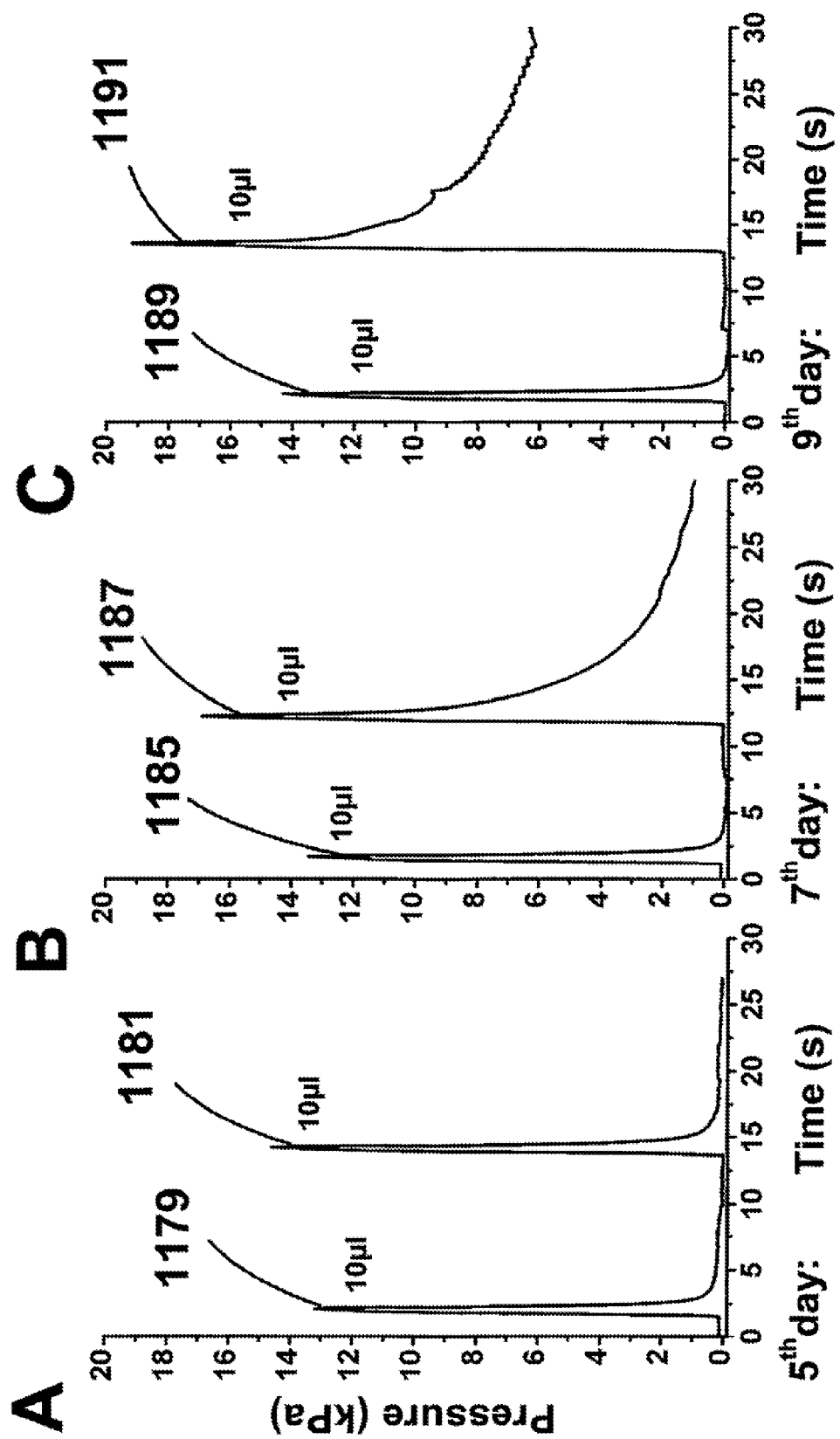
FIGS. 11A, 11B, 11C, 11D illustrate results of pressure measurements performed in a healthy subject over an extended time period of 9 days by one of the arrangements illustrated in FIG. 1, 2 or 3 according to an embodiment of the present invention.

FIGS. 11A, 11B, 11C illustrate results of pressure measurements performed in a healthy subject over an extended time period of 9 days.

In particular, FIGS. 11A to 11C illustrate further measurement results of pressure time courses obtained during administering a saline solution (NaCl) into an organism using a cannula. Thereby, the measurement results illustrated in FIG. 11A have been obtained at the fifth day after insertion of the cannula, the measurement results illustrated in FIG. 11B have been obtained at the seventh day after insertion of the cannula and the measurement results illustrated in FIG. 11C having obtained at the ninth day after insertion of the cannula. Thereby, in FIGS. 11A to 11C, the time courses 1179, 1185, 1189 illustrate the situation, when one end of the cannula is external to the tissue (thus representing a second pressure measurement) and the time courses 1181, 1187 and 1191 represent the situation, when one end of the cannula is inserted into the organism (thus representing a second measurement, respectively). In all cases a fluid volume of 10 μl was applied and thus administered into the organism.

The measurement results illustrated in FIGS. 11A to 11C may be utilized in order to derive information indicative of a tissue resistance against flow of a fluid upon administration into the tissue and the information indicative of the tissue resistance may be used by a controller such as a controller of the arrangements illustrated in FIG. 1, 2 or 3 in order to adjust an administration characteristics of the fluid administered into the organism.

Figure 12:
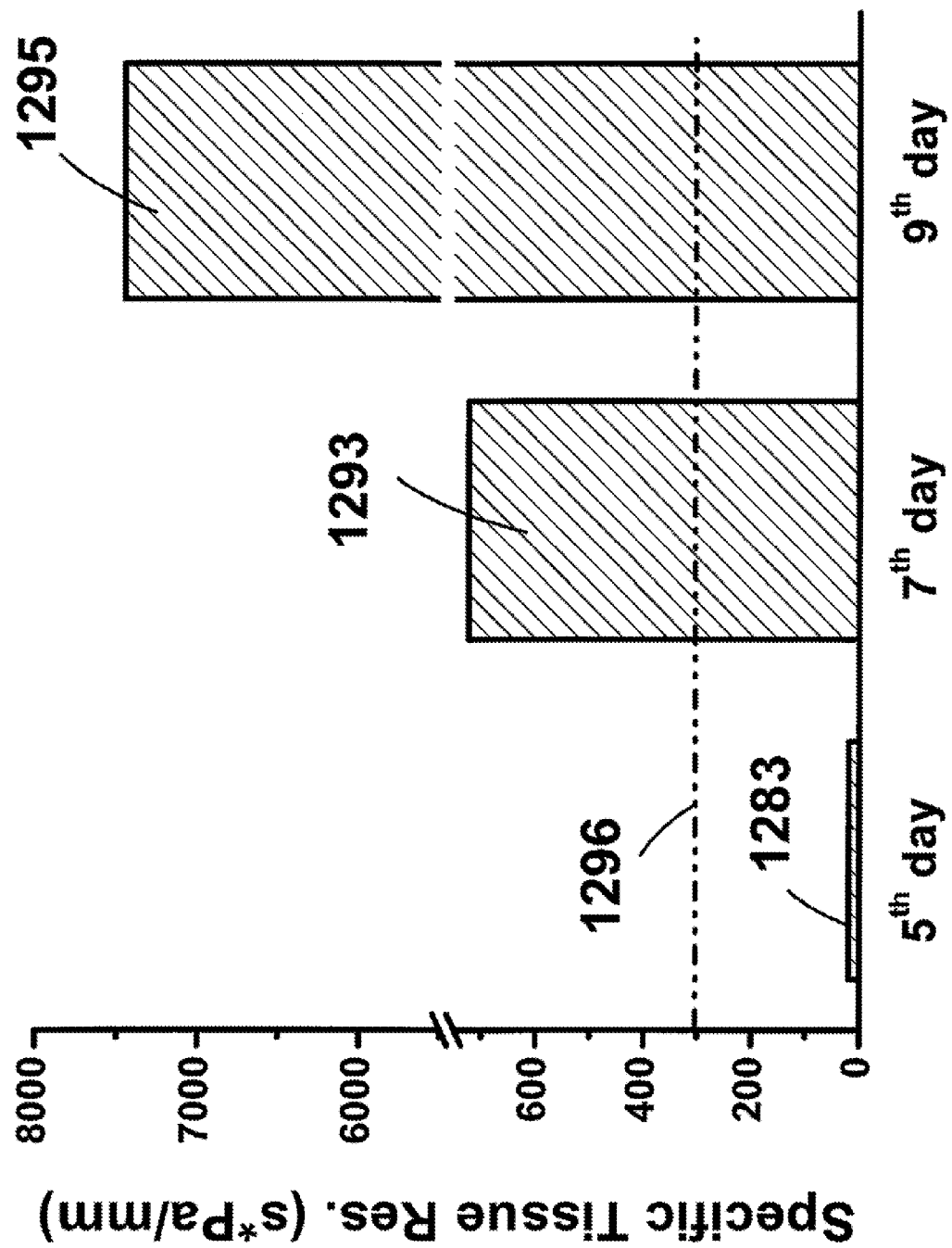
FIG. 12 illustrates specific tissue resistance values of a healthy subject measured over an extended time period of 9 days with one of the arrangements illustrated in FIG. 1, 2 or 3 according to an embodiment of the present invention.

FIG. 12 illustrates specific tissue resistances (columns 1283, 1293 and 1295) calculated from the observed differences of the pairs of pressure values (1181, 1179); (1187, 1185) and (1191, 1189) illustrated in FIGS. 11A-11C, applied flow rates, and the cross-sectional area of the used cannula 317.

In particular, FIG. 12 illustrates evaluation results of the pressure time courses illustrated in FIGS. 11A to 11C according to an embodiment of the present invention which may for example be performed by the arrangements illustrated in FIG. 1, 2 or 3. As in the evaluation results illustrated in FIG. 10, the columns 1283, 1293, 1295 represent specific tissue resistances which are calculated from the pairs of measurement illustrated in FIGS. 11A to 11C, respectively. In particular, a difference between the area under the curve 1181 and the area under the curve 1179 was formed and divided by the amount of the administered fluid and divided by the cross-sectional area of the cannula in order to derive the tissue resistance or specific tissue resistance 1283 illustrated in FIG. 12.

As can be taken from FIG. 12, the tissue resistance at the fifth day (column 1283) after insertion of the cannula is much smaller than the tissue resistance (column 1293) at the seventh day after insertion of the cannula which is in turn much smaller than the tissue resistance (1295) at the ninth day after insertion of the cannula, thereby indicating that the tissue resistance strongly increased.

The horizontal line 1296 represents an exemplary threshold specific tissue resistance which may be used as a criterion to decide when an anatomical location for administering the fluid should be changed. In particular, the value of the threshold 1296 may be determined based on a relationship between an absorbance of the fluid and the specific tissue resistance. If adaptation or alteration of exogenous factors does not allow adjustment of the absorption rate to be a demanded or desired absorption rate, a particular associated specific tissue resistance may be too high, such that it may be advisable to change the administration location at the tissue. This specific tissue resistance may be chosen as the threshold 1296 according to an embodiment of the present invention.

In particular, the tissue resistance, after a prolonged use of the administration site, may exceed the threshold value 1296, above which adjustments the bolus length, pulse duration, pulse height, pulse frequency and/or pulse shape may not be sufficient anymore to achieve a desired absorption rate of the substance. Thus, if the threshold 1296 is reached (after a particular wear time of the cannula at the same anatomical location) the controller of the arrangements as illustrated in FIG. 1, 2 or 3 may be adapted to inform the user (by for example presenting an indication) that the maximum duration of the use of the administration site (or the anatomical location of the organism) has been reached and that the location of the administration site should be changed in order to achieve the desired substance absorption rate again at another anatomical location of the insertion site of the cannula.

It can be taken from FIG. 12 that the tissue resistance increases for increased duration of wearing the cannula. In order to decide whether to change the anatomical location where the cannula is inserted, a threshold 1296 may be employed. When the measured or evaluated or derived specific tissue resistance exceeds the threshold 1296, the controller of the arrangement as illustrated in FIG. 1, 2 or 3 may indicate to the user that the anatomical location at which the cannula is inserted and via which the fluid is administered into the organism, should be changed, in order to reach a desired absorption rate of the substance contained in the fluid at another new anatomical location where the cannula (or a new cannula) should be inserted.

Figure 13:
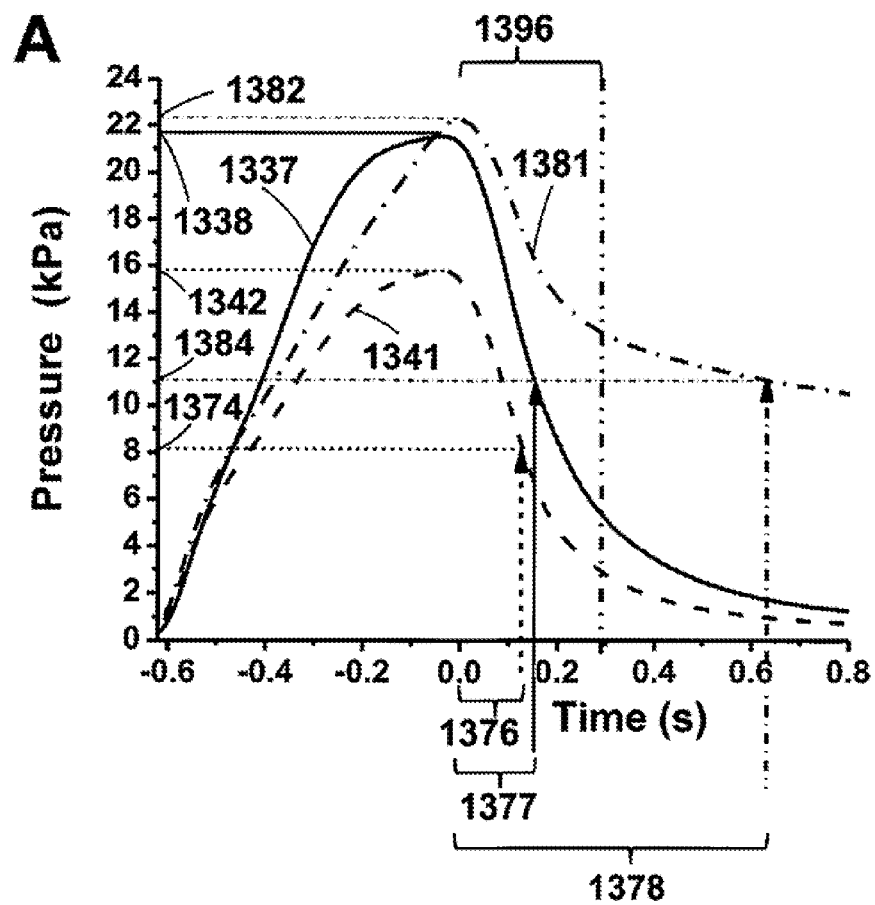
FIGS. 13A, 13B illustrate pressure time courses from a diabetic subject measured by one of the arrangements illustrated in FIG. 1, 2 or 3 according to an embodiment of the present invention.
Figure 13:
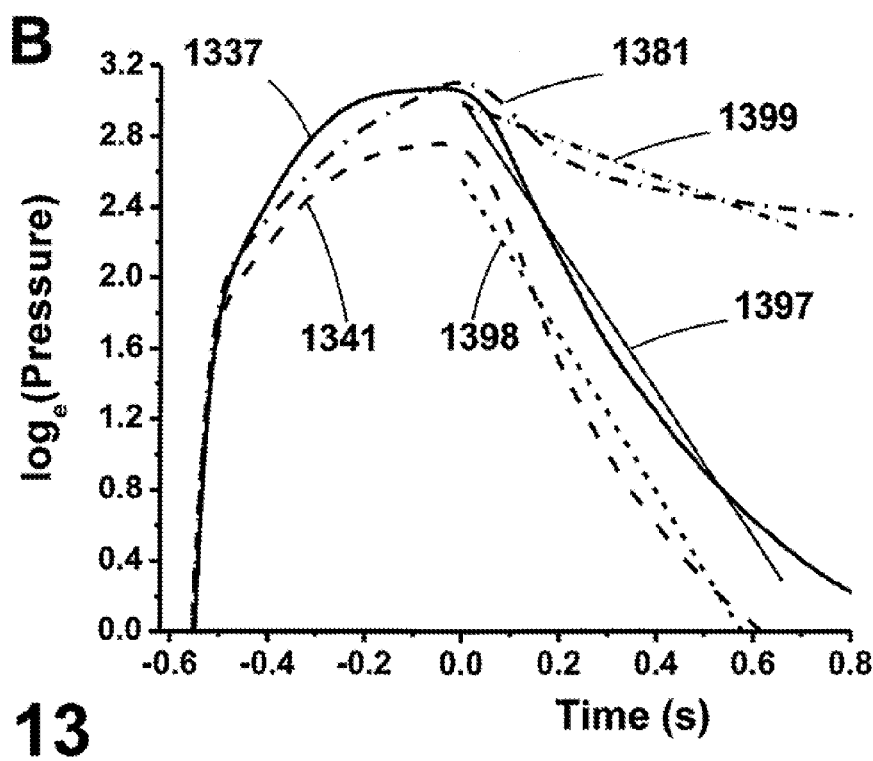

FIGS. 13A, 13B illustrate pressure time courses obtained by performing the first measurement in a diabetic subject after 0 h (1337), 24 h (1341), and 120 h (1381) of infusion site use.

In particular, FIG. 13A and FIG. 13B illustrate alternative procedures how to decide when an administration site should be changed. The procedures illustrated and described below and depicted in FIGS. 13A and 13B may for example be performed by the arrangements illustrated in FIGS. 1, 2 and/or 3 according to an embodiment of the present invention.

The abscissas in FIGS. 13A and 13B indicate the time while ordinates indicate the pressure of the fluid administered into the tissue of the organism. The pressure time courses 1337, 1341 and 1381 correspond (are equal to) the pressure time courses 937, 941 and 981 illustrated in FIGS. 9A, 9B and 9D but are indicated in a somewhat stretched manner (stretched in the time direction), in order to in more detail depict their shapes.

The pressure curve 1337 has a maximum 1338, the pressure curve 1341 has a maximum 1342 and the pressure curve 1381 has a maximum 1382. According to the evaluation method illustrated in FIG. 13A the maximum values 1338, 1342 and 1382 are obtained or calculated from the pressure curves 1337, 1341 and 1381, respectively. Further, the time intervals 1376, 1377 and 1378 which are defined as the respective times it takes for the pressure to decay to a certain percentage of the its maximum value, such as a percentage of 50% (or other percentages such as 10%, 25%, 66%, 33% or 75%) are obtained or calculated from the pressure curves 1341, 1337 and 1381, respectively.

In particular, in FIG. 13A, for each pressure time course, the time for the pressure to decay to 50% of its maximal value was calculated ($t_{50\%}$; in s).

In the illustrated example, after a time interval 1376, the pressure curve 1341 has declined to 50% (1374) of the maximum value 1342. However, the pressure curve 1381 taken 120 hours after inserting the cannula into the organism reaches after a time interval 1378 50% (1384) of its maximum value 1382, wherein the time interval 1378 is much larger than the time interval 1376. The duration of the respective time interval 1376, 1377 or 1378 may correlate or may even be proportional to a specific tissue resistance. Thus, the time intervals which are required for the pressure to decline to a particular fraction of its maximum value may be indicative (or may be even proportional or may at least correlate with) the specific tissue resistance and thus these time intervals may be utilized or employed by the arrangements illustrated in FIG. 1, 2 or 3 in order to derive information indicative of the tissue resistance. Further, this information about the tissue resistance may later on be used to adapt an administration characteristic of the fluid based on the information.

Further, a threshold time interval, such as threshold time interval 1396 illustrated in FIG. 13A may be defined. According to an embodiment of the present invention, if the time interval which is required for the pressure to decline to a particular percentage of its maximum value exceeds the threshold time interval 1396, the arrangement illustrated in FIG. 1, 2 or 3 may indicate to the user that the anatomical location at which the cannula is inserted for administering the fluid should be changed.

FIG. 13B illustrates a further evaluation method for evaluating pressure time curves as illustrated in FIGS. 9A, 9B and 9D according to an embodiment of the present invention which may be carried out by the arrangement as is illustrated in FIG. 1, 2 or 3. On an abscissa the time is indicated while on an ordinate the logarithm of the pressure is indicated. The curves 1337, 1341 and 1381 in FIG. 13B correspond to the curves 1337, 1341 and 1381, respectively of FIG. 13A.

In a first approximation a decline of the pressure with time may be described by an exponential function which may be defined by a coefficient within the exponential function which is multiplied with time. In the logarithmic illustration illustrated in FIG. 13B an ideal logarithmic function would become a straight line whose inclination indicates the coefficient within the exponential function. For example, the straight line 1397, 1398 and 1399 may approximate inclinations of the pressure curves 1337, 1341 and 1381, respectively. Further, the steepness of the straight lines 1397, 1398 and 1399 may be interpreted an indication of the specific tissue resistance according to this embodiment. Further, there may be a threshold inclination defined and when this threshold inclination is superseded the arrangements as illustrated in FIG. 1, 2 or 3 may indicate to the user that the tissue resistance exceeds a value which does not allow achievement of the desired absorption rate. Thus, in this case the arrangements as illustrated in FIG. 1, 2 or 3 may indicate to the user that the anatomical location of the tissue at which the cannula is inserted should be changed in order to achieve administration of the fluid into the organism with the desired absorption rate of the substance contained in the fluid.

In particular, in FIG. 13B a one-exponential function was fit to each of the pressure time courses observed. The form of the one-exponential for fitting the data was: $P(t)=P_0 e^{-k\,t}$, where k is the slope, P(t) is the pressure at time t, and $P_0$ is the pressure at time zero. For identification of the parameters $P_0$ and k, the observed pressure data were first transformed applying the natural logarithm function, and then a linear regression was performed using the transformed pressure data set from 0 to 0.65 s. Other fitting procedures are possibly employed by the arrangements illustrated in FIG. 1, 2, or 3.

The derived parameters (k and $t_{50\%}$) may strongly correlate with the obtained specific tissue resistances (compare FIG. 10) and, therefore, may alternatively be used to monitor the tissue resistance during infusion site use.

Embodiments of the present invention may take advantage of the following findings by the inventor:

The velocity with which a desired amount of insulin solution is infused into the tissue (i.e. the duration of insulin bolus) influences both the spatial distribution of the infused insulin in the tissue and the subsequent transport of the insulin from the infusion site to the blood (insulin absorption).

The resistance exerted by the tissue upon (or against) the insulin solution entering the tissue (i.e. tissue resistance reflecting morphological and structural properties of the tissue as well as tissue-specific transport properties for the insulin solution) varies from infusion site to infusion site and also depends on the length of the use of the infusion site. Furthermore, the spatial tissue distribution and absorption of the infused insulin are inversely dependent on the tissue resistance.

Reduced insulin absorption during prolonged use of an infusion site may be detected by the measurement of the tissue resistance. A too low insulin absorption during infusion site use may indicate that the maximum duration of the infusion site use is reached and that a new infusion site should be established.

Embodiments of the present invention take advantage of the finding by the inventor that the hydraulic resistance or tissue resistance at the site of the insulin infusion may be determined (in particular based on pressure measurements) and that the flow velocity or flow rate (bolus length and infusion rate) by which the insulin solution is delivered to the tissue may be adjusted based on the measured tissue resistance, so as to achieve an insulin absorption rate as high as possible and to minimize the variability of the insulin absorption and insulin action. Furthermore, by monitoring the tissue resistance, the maximum duration of use of an infusion site may be determined.

It should be noted that the term "comprising" does not exclude other elements or steps and the "a" or "an" does not exclude a plurality. Also elements described in association with different embodiments may be combined.

The invention claimed is:

1. An arrangement for administering a predetermined amount of a substance into an organism, the arrangement comprising:

a member adapted to provide information indicative of a tissue resistance against flow of a fluid containing the substance upon administration into the tissue;

a controller adapted to adjust an administration characteristic of the fluid based on the information such as to achieve an intended absorption rate of the substance;

a pump adapted to be coupled to a reservoir of the fluid and adapted to drive the fluid;

a conduit, in particular comprising a flexible tubing, for guiding the fluid drive by the PUMP from the reservoir into the tissue, the conduit having one end, a cannula, insertable into the tissue and having another end coupled to the pump unit;

wherein the controller is adapted to control the pump to adjust the flow rate of the fluid to comply with the adjusted administration characteristic;

wherein the member comprises a pressure sensor and is adapted to measure a pressure of the fluid in the conduit;

wherein the arrangement is adapted, using the pressure sensor, to determine a pressure difference based on a first pressure measurement, when the cannula is inserted into the tissue; and a second pressure measurement, when the cannula is external to the tissue at atmospheric pressure.

2. The arrangement according to claim 1, wherein the administration characteristic comprises at least one definition of an exogenous factor comprising:
- a total administration duration being a total time duration over which fluid is continuously or repeatedly in a pulse wise manner administered;
- an administration pulse duration being a time interval over which fluid is continuously administered with a particular flow rate;
- an administration pulse height being a flow rate with which the fluid is continuously administered during the administration pulse duration;
- an administration pulse frequency being the number of administration pulses per time unit used to administer the fluid during the total administration duration;
- an administration pulse shape being a time course of a flow rate with which the fluid is administered during the administration pulse duration;
- an anatomical location of the administration site where the fluid is administered into the organism; or
- a duration of use of the administration site for administering the fluid into the organism.

3. The arrangement according to claim 1, wherein the information indicative of the tissue resistance comprises at least one of:
- a time interval in which a pressure decreases to a predetermined fraction of a maximum pressure during an administration pulse;
- a steepness of a decline at which the pressure decreases from a maximum pressure during an administration pulse; and
- a value of the tissue resistance, in particular maximum value during an administration pulse,
- wherein the tissue resistance is in particular derived from a pressure measurement, further in particular proportional to an area under a pressure curve, during an administration pulse.

4. The arrangement according to claim 3, wherein the arrangement is adapted to indicate to a user that the administration site should be changed, if the information indicative of the tissue resistance satisfies a criterion, wherein the criterion comprises at least one of:
- a time interval threshold;
- a steepness threshold; or
- a tissue resistance threshold.

5. The arrangement according to claim 1, wherein the pressure sensor is located
- at the pump;
- at the reservoir; or
- at a location along the conduit, in particular at or close to the one end or the other end.

6. The arrangement according to claim 1,
wherein the arrangement is further adapted to obtain the tissue resistance based on the determined pressure difference, as a time average of the pressure difference, taking into account a hydrostatic pressure of the liquid during the first pressure measurement and/or the second pressure measurement.

7. The arrangement according to claim 6, wherein the second measurement is performed:
- at an instance not related to administration of the substance, in particular at a manufacturer site, and/or
- in a time window, in particular between 0 s and 10 min, before inserting the cannula into the organism, and/or wherein the first measurement is performed:
- during basal administration of the substance, and/or
- at a beginning of a bolus administration of the substance, in particular during 1 to 10 pulses during a first 1 to 50 pulses of the bolus administration,
- wherein the controller is in particular adapted to adjust the flow rate during the first measurement and during the second measurement to a same value.

8. The arrangement according to claim 1, wherein the arrangement is adapted to increase the flow rate when the tissue resistance increases, in order to achieve the intended absorption rate of the substance, when administering the predetermined amount of the substance.

9. The arrangement according to claim 1, wherein a relationship between the absorption rate of the substance and the tissue resistance, in particular depending on controllable extrinsic covariates comprising a total administration duration, administration pulse duration, administration pulse height, administration pulse frequency, administration pulse shape, anatomical location of the administration site and/or duration of use of conduit and administration site has been determined previously, in particular taking into account intrinsic covariates comprising gender, age, body weight, body-mass-index, body surface area, and/or skinfold thickness,
wherein the controlling of flow rate of the fluid is further based on the previously determined relationship and at least one of the covariate values.

10. The arrangement according to claim 1, wherein the intended absorption rate has been determined based on
- an appearance study, in particular concentration measurements, of the substance, in particular insulin, in particular in the blood; and/or
- a disappearance study of the substance, in particular comprising labeling the substance with an radioactive isotope; and/or
- a metabolic effect of the substance, in particular an infusion rate of a further substance, in particular a sugar, conveyed into the organism, in order to keep a concentration of the further substance constant.

11. The arrangement according to claim 1,
wherein the controller is adapted to control the administration characteristic based on a changing tissue resistance time.

12. The arrangement according to claim 1, wherein the member comprises:
- a storage medium storing the information, the information being based on at least one previous measurement of the tissue resistance, in particular in dependence of a set of covariates, wherein the set of covariates comprises a duration of use of the administration site and conduit and/or tissue type and/or insertion location and/or insertion region within the tissue and/or conduit insertion depth and/or time of day and/or gender and/or age and/or weight and/or height and/or body-mass-index and/or body-surface area and/or skinfold thickness,
wherein obtaining the information comprises:
accessing the information in the storage medium.

13. The arrangement according to claim 1,
wherein the substance comprises insulin and the fluid is an aqueous insulin solution,
wherein in particular the conduit is adapted to be inserted at the one end into the cutaneous or subcutaneous tissue of a human.

14. A method, comprising:
providing a system including:
- a member adapted to provide information indicative of a tissue resistance against flow of a fluid containing the substance upon administration into the tissue;
- a controller adapted to adjust an administration characteristic of the fluid based on the information such as to achieve an intended absorption rate of the substance;
- a pump adapted to be coupled to a reservoir of the fluid and adapted to drive the fluid;
- a conduit, in particular comprising a flexible tubing, for guiding the fluid drive by the PUMP from the reservoir into the tissue, the conduit having one end, a cannula, inserterable into the tissue and having another end coupled to the pump unit;
- wherein the controller is adapted to control the pump to adjust the flow rate of the fluid to comply with the adjusted administration characteristic;
- wherein the member comprises a pressure sensor and is adapted to measure a pressure of the fluid in the conduit;

performing a first pressure measurement with a pressure sensor, when a cannula is inserted into a tissue; of an organism;

performing a second pressure measurement with the pressure sensor, when the cannula is external to the tissue at atmospheric pressure;

determining a pressure difference from the first pressure measurement and the second pressure measurement with a controller arranged to receive the first pressure measurement and the second pressure measurement from the pressure sensor.

15. The method of claim 14, further comprising:

providing information indicative of a tissue resistance against flow of a fluid containing a substance upon administration into the tissue; and adjusting an administration characteristic of the fluid based on the information such as to achieve an intended absorption rate of the substance.

16. The method according to claim 15, wherein adjusting is performed at times when a blood glucose concentration of the organism is between 1.05 and 5 times a target level and/or in a time interval 1 sec to 30 min before ingestion of a meal received by the organism.

* * * * *